(12) United States Patent
Fujii et al.

(10) Patent No.: US 10,794,799 B2
(45) Date of Patent: Oct. 6, 2020

(54) OPEN EMISSION ANALYSIS METHOD AND DEVICE

(71) Applicant: HONDA MOTOR CO., LTD., Minato-Ku, Tokyo (JP)

(72) Inventors: Satoshi Fujii, Aso (JP); Takuma Okonogi, Ozu-machi (JP); Hideo Nihei, Tokyo (JP)

(73) Assignee: Honda Motor Co., Ltd., Tokyo (JP)

( * ) Notice: Subject to any disclaimer, the term of this patent is extended or adjusted under 35 U.S.C. 154(b) by 280 days.

(21) Appl. No.: 16/083,278

(22) PCT Filed: Feb. 28, 2017

(86) PCT No.: PCT/JP2017/008020
§ 371 (c)(1),
(2) Date: Sep. 7, 2018

(87) PCT Pub. No.: WO2017/154688
PCT Pub. Date: Sep. 14, 2017

(65) Prior Publication Data
US 2019/0101474 A1 Apr. 4, 2019

(30) Foreign Application Priority Data
Mar. 9, 2016 (JP) .............................. JP2016-046374

(51) Int. Cl.
*G01N 1/22* (2006.01)
*F01N 3/00* (2006.01)
(Continued)

(52) U.S. Cl.
CPC .............. *G01N 1/2252* (2013.01); *F01N 3/00* (2013.01); *F01N 3/105* (2013.01); *G01N 1/38* (2013.01);
(Continued)

(58) Field of Classification Search
CPC ......... G01N 1/2252; G01N 2001/2255; G01N 33/0018; F01N 2590/04; F01N 3/00;
(Continued)

(56) References Cited

U.S. PATENT DOCUMENTS 5,907,109 A * 5/1999 Tedeschi .................. G01N 1/26
73/864.73
6,085,582 A * 7/2000 Tripathi .............. G01M 15/102
73/114.71
(Continued)

FOREIGN PATENT DOCUMENTS

CN 104568518 A 4/2015
JP H03-154845 A 7/1991
(Continued)

OTHER PUBLICATIONS

Extended European search report dated Feb. 21, 2019 issued in the corresponding EP Patent Application No. 17763028.2.
(Continued)

*Primary Examiner* — Francis C Gray
(74) *Attorney, Agent, or Firm* — Carter Blackman & Associates, P.C.; Joseph P. Carrier; William D. Blackman

(57) ABSTRACT

A filter made of a sponge material having air permeability and elasticity is interposed between an exhaust port of an exhaust gas sampling unit and a sampling port to thereby close a gap between the exhaust port and the sampling port. In this state, when the exhaust gas sampling unit is suctioned at a constant flow rate, the exhaust gas and the outside air around the exhaust port are taken into the exhaust gas sampling unit from the sampling port. At this time, the flow rate of the outside air taken in through the filter is suppressed by the air-flow resistance of the filter, and therefore the total flow rate of the exhaust gas and the outside air taken into the exhaust gas sampling unit is caused to be less than the
(Continued)

suction flow rate, thereby simply and reliably preventing the exhaust gas from leaking out.

10 Claims, 12 Drawing Sheets

(51) Int. Cl.
  *G01N 33/00* (2006.01)
  *G01N 1/38* (2006.01)
  *F01N 3/10* (2006.01)
(52) U.S. Cl.
  CPC . *G01N 33/0018* (2013.01); *G01N 2001/2255* (2013.01)
(58) Field of Classification Search
  CPC ....... F01N 3/105; G01M 3/002; G01M 15/02; G01M 15/102
  See application file for complete search history.

(56) References Cited

U.S. PATENT DOCUMENTS

| | | | | |
|---|---|---|---|---|
| 7,071,002 | B1* | 7/2006 | Tefft | G01M 15/102 422/83 |
| 7,946,160 | B2* | 5/2011 | LaPree | G01M 15/02 73/114.71 |
| 2014/0338426 | A1* | 11/2014 | Noda | F01N 11/00 73/40 |
| 2015/0107330 | A1 | 4/2015 | Yokoyama et al. | |
| 2015/0300927 | A1* | 10/2015 | Easton | G01N 27/622 73/863.52 |
| 2017/0167351 | A1* | 6/2017 | Kumagai | F01N 13/008 |
| 2019/0094110 | A1* | 3/2019 | Fujii | G01N 1/00 |

FOREIGN PATENT DOCUMENTS

| | | |
|---|---|---|
| JP | H04-331890 A | 11/1992 |
| JP | H11-201877 A | 7/1999 |
| JP | H11-201879 A | 7/1999 |
| JP | 2012-083205 A | 4/2012 |
| JP | 2015-081804 A | 4/2015 |
| WO | 02/071030 A1 | 9/2002 |

OTHER PUBLICATIONS

Office Action issued in the corresponding Chinese Patent Application No. 201780011315.8 dated Mar. 17, 2020.
PCT/ISA/210 from International application PCT/JP2017/008020 with the English translation thereof.

* cited by examiner

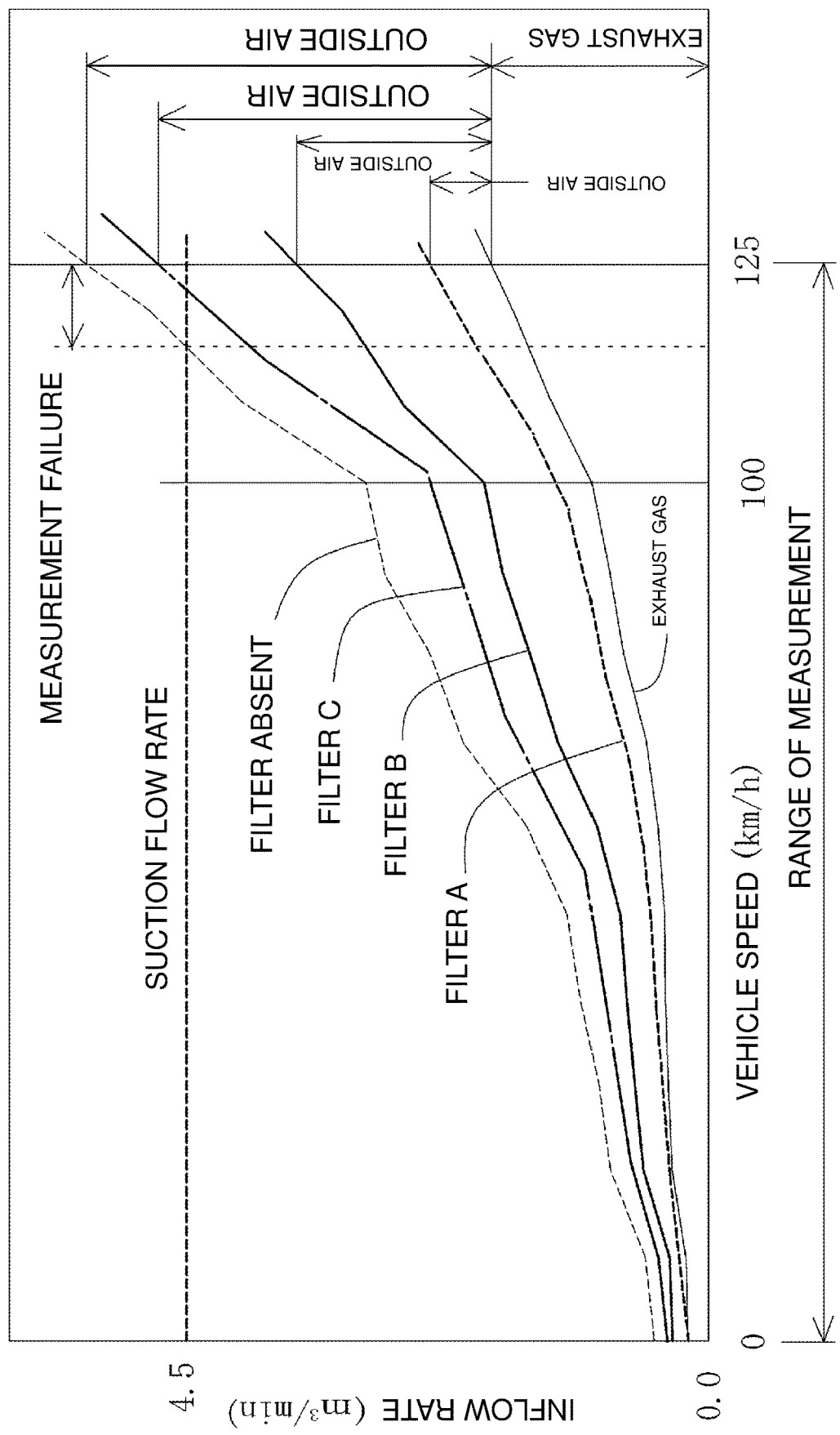

FIG. 12A 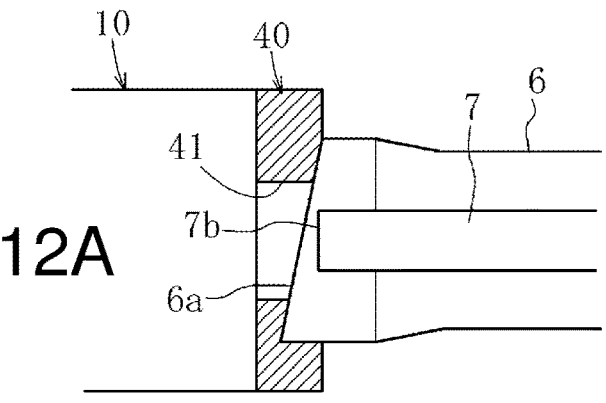 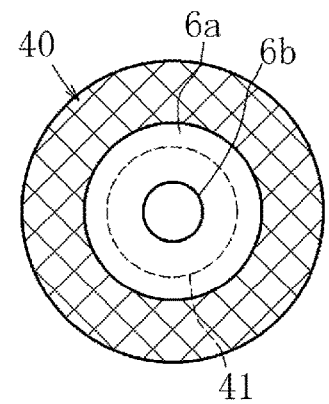
FIG. 12B 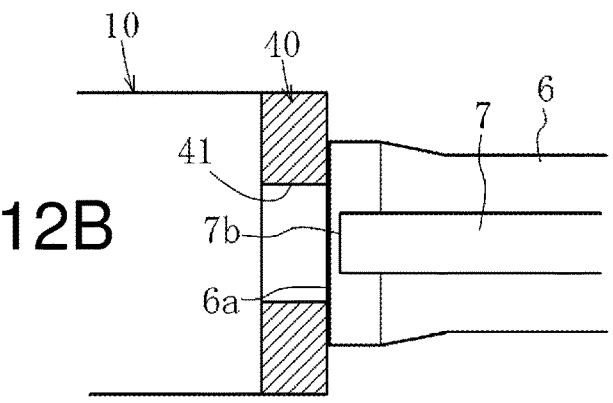 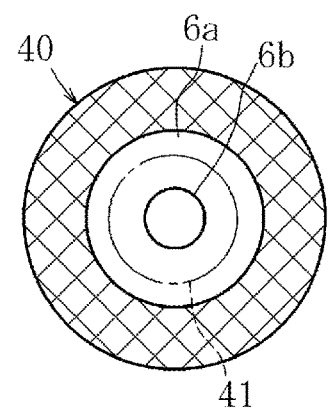
FIG. 12C 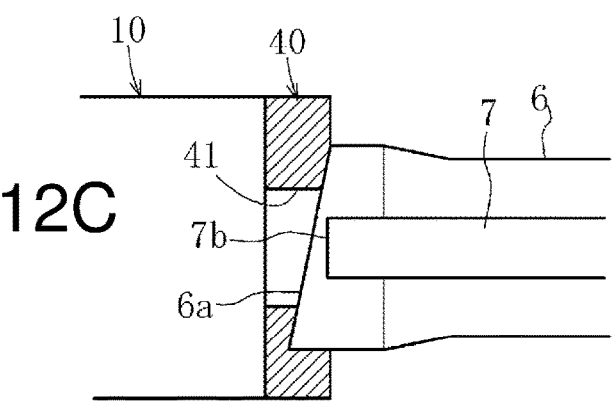 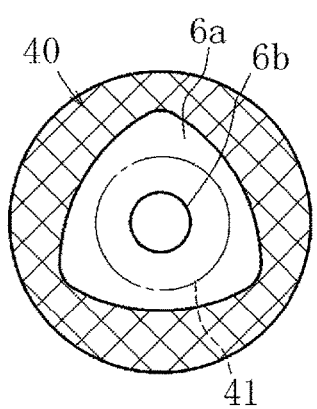
FIG. 12D 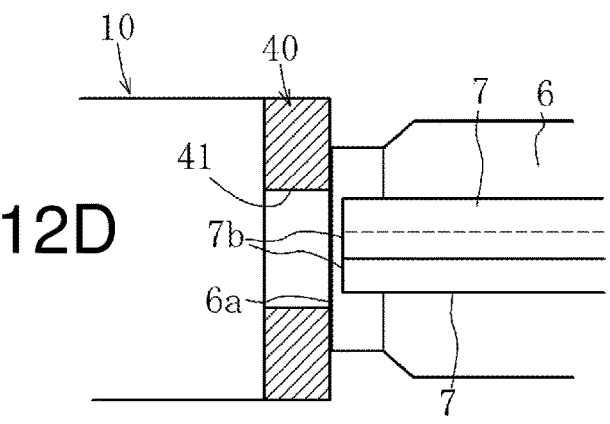 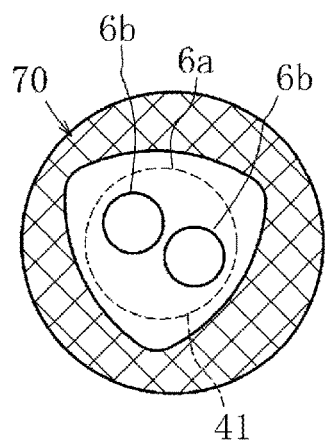

OPEN EMISSION ANALYSIS METHOD AND DEVICE

FIELD

The present invention relates to a method and a device in an open exhaust gas analysis (open emission analysis) for analyzing component concentrations in the exhaust gas of a vehicle.

BACKGROUND

When measuring a concentration of a substance contained in exhaust gas, a closed type exhaust gas analysis (close emission analysis) is known in which an exhaust port faces a sampling port of an exhaust gas sampling unit and the sampling port and the exhaust port are connected in a state where a gap located between the sampling port and the exhaust port is airtightly covered to thereby collect and analyze all the exhaust gas. As an example of this analyzing device, the gap between the sampling port and the exhaust port is covered hermetically with a hollow emission boot in order to prevent exhaust gas from leaking out into the surrounding atmosphere through the gap, and conversely, to prevent the surrounding atmosphere from flowing into the sampling port through the gap.

An open emission analysis is also known in which an outside air inflow gap is provided around the sampling port and the exhaust port, and the exhaust gas and the outside air around the exhaust port are collected and aspirated together for concentration analysis. Although the open emission analysis enables measurement at a state that is close to the actual running state of the vehicle, it is necessary to take in the whole amount and prevent leakage of the exhaust gas.

Therefore, as an example of preventing such leakage, a slit is provided in the exhaust gas sampling unit in the vicinity of the sampling port, and when the flow of the cooling wind (outside air blown as the traveling wind from a blower of a measuring device) flowing around is uneven, some of the fast cooling wind is caused to flow to the outside from the slit so that the exhaust gas is entrained by this fast cooling wind thereby preventing the exhaust gas from leaking out from the sampling port (see Patent Literature 1).

CITATION LIST

Patent Literature

Japanese Unexamined Patent Application, Publication No. 2015-81804

BRIEF SUMMARY

Technical Problem

In the above described close emission analysis, the following inconveniences occur due to the emission boot being covered with a muffler and the periphery thereof is tightened with a band so as to be airtightly connected. The inconveniences include: preventing damage to the muffler is required when installing the emission boot with a fact that basically the emission boots can only be attached to a cylindrical muffler; parts on the outer periphery of the muffler provided in the section where the emission boot is to be mounted must be removed beforehand and these parts must be detached in a way so as not to cause damage to the muffler; a connecting jig exclusive for each model is required between the muffler and the sampling port and therefore a large number of connecting jigs corresponding to all models of the object to be measured must be prepared in advance as stocks, but at the time of actually performing the measurement, the corresponding items must be sorted out from this stock.

The aforementioned close emissions analysis is capable of preventing leakage of exhaust gas but requires much time and labor for measurement. Therefore, there is a demand for a versatile method and device that is less troublesome and not influenced by the shape of the muffler.

On the other hand, according to the open emission analysis method disclosed in Patent Literature 1, when traveling wind having uneven flow velocity occurs around the sampling port, leaking out of the exhaust gas that is entrained by the fast traveling wind can be prevented. However, as a result of research, the inventor of the present application found that the leakage cannot be prevented when the flow rate of outside air consisting of the traveling wind and atmosphere to be taken into the sampling port becomes large to some extent. This will be explained in the following.

FIG. 10 is a view illustrating the relationship between the total amount of inflow of the outside air flow rate and the exhaust gas flow rate taken into the sampling port and the suction flow rate to be aspirated from the vicinity of the sampling port by a suction blower, etc. FIG. 10A is a view illustrating the conventional open emission analysis method.

In FIG. 10A, an exhaust port 7a of a tail pipe 7 protruding from a muffler 6 is located in the vicinity of a sampling port 11 of an exhaust gas sampling unit 10, and an outside air inflow gap communicating with the surrounding atmosphere is formed between the exhaust port 7a and the sampling port 11. The exhaust gas sampling unit 10 is sucked at a constant flow rate by a suction blower or the like (not shown) through a quantitative flow path 20.

On the other hand, traveling wind (corresponding to a part of the outside air) is blown from a blowing fan (not shown) toward the sampling port 11, some of which flows outside of the exhaust gas sampling unit 10 as indicated by an arrow A, while some flows into the exhaust gas sampling unit 10 together with the surrounding atmosphere as indicated by an arrow B. Note that the air volume of the traveling wind changes so as to become larger as the vehicle speed increases. Further, the exhaust gas discharged from the exhaust port 7a flows from the sampling port 11 to the inside of the exhaust gas sampling unit 10 as indicated by an arrow C. The flow rate of the exhaust gas also changes according to the vehicle speed.

In this configuration, when the vehicle speed increases and the total inflow flow rate of the outside air and the exhaust gas increases, leakage of exhaust gas occurs. For example, the total inflow flow rate indicated by the broken line in FIG. 8 in the conventional method exceeds the suction flow rate around at 120 km/h in the high speed range where the vehicle speed is close to the measurement limit, but at this time, when some of the outside air is bounced back as shown in FIG. 10A, a portion of the exhaust gas is entrained in this rebound and therefore leaks out from the sampling port 11 as indicated by an arrow D.

It was found that the cause of this leakage is based on the fact that the sum of the flow rate of the exhaust gas and the flow rate of the traveling wind generates an excessive flow rate G at which the flow rate becomes larger than the suction flow rate in the high speed range or the like.

Therefore, with respect to a structure wherein such an excessive flow rate G is generated, leakage cannot be prevented even if the above-mentioned slit is provided.

Particularly, the prevention of leakage has been difficult in the high speed range where the total inflow flow rate rises.

The present invention has been made in order to accomplish an objective of providing a method and device capable of reducing leakage, such as the close emission analysis, while having versatility but less troublesome in an open emission analysis.

Solution to Problem

In order to solve the above-mentioned problem, the invention of an open emission analysis method according to a first aspect thereof is an open emission analysis method, including taking in exhaust gas discharged from an exhaust port (7a) together with ambient outside air from an exhaust gas sampling unit (10);

analyzing the collected exhaust gas;

covering an outside air inflow gap by an air-permeable outside air inflow suppressing member (40) located between a sampling port (11) of the exhaust gas sampling unit (10) and a periphery of the exhaust port (7a); and suppressing inflow of the outside air by the outside air inflow suppressing member (40) in order to prevent leakage of the exhaust gas from the sampling port (11).

The invention according to a second aspect thereof further includes, in the above first aspect, suctioning the exhaust gas sampling unit (10) at a predetermined suction flow rate, and suppressing the total inflow flow rate of the exhaust gas and the outside air flowing into the sampling port (11) to be less than the suction flow rate by using the outside air inflow suppressing member (40).

The invention according to a third aspect thereof is characterized in that, in the above second aspect, the outside air inflow suppressing member (40) allows the exhaust gas to flow without interfering and the outside air to pass through while suppressing the speed of the air by air-flow resistance.

The invention of an open emission analysis device according to a fourth aspect thereof is an open emission analysis device including:

an exhaust gas sampling unit (10) for taking in exhaust gas discharged from an exhaust port (7a) located at a rear end portion of a muffler (6) together with ambient outside air;

a quantitative flow path (20) for flowing a mixed gas of the collected exhaust gas and outside air at a constant flow rate;

a suction means (24) for sucking the quantitative flow path (20) at a predetermined suction flow rate;

a concentration analyzing unit (30) for analyzing the exhaust gas with respect to the mixed gas in the quantitative flow path (20); and an air-permeable outside air inflow suppressing member (40) configured to cover an outside air inflow gap located between a sampling port (11) of the exhaust gas sampling unit (10) and a periphery of the exhaust port (7a), wherein the outside air inflow suppressing member (40) passes the outside air therethrough to the sampling port (11).

The invention according to a fifth aspect thereof is characterized in that, in the above fourth aspect, the outside air inflow suppressing member (40) is a filter (40) covering the sampling port (11) and has a through hole (41) serving as an exhaust gas passage (44), and the exhaust port (7a) faces the through hole (41).

The invention according to a sixth aspect thereof is characterized in that, in the above fifth aspect, the muffler (6) includes an end cap (6a) covering a rear end portion thereof, and the outside air inflow suppressing member (40) is disposed between the sampling port (11) and the end cap (6a).

The invention according to a seventh aspect thereof further includes, in the above sixth aspect, a curved portion (15) that is a turned-back edge portion of the sampling port (11A), wherein the outside air inflow suppressing member is disposed between the curved portion (15) and the end cap (6a).

The invention according to an eighth aspect thereof is characterized in that, in any one of the above fourth through seventh aspects, the outside air inflow suppressing member (40) is made of a material that is deformable in shape.

The invention according to a ninth aspect thereof is characterized in that, in the above fifth aspect, the filter (40) is made of a sponge material whose air permeability changes according to the roughness of the sponge material.

The invention according to a tenth aspect thereof is characterized in that, in the above ninth aspect, the roughness of the sponge material renders the total inflow flow rate of the exhaust gas and the outside air flowing into the sampling port (11) to be set less than the suction flow rate in an entire measurement range.

Advantageous Effects

According to the invention of the first aspect, since the outside air inflow gap located between the sampling port (11) of the exhaust gas sampling unit (10) and the periphery of the exhaust port (7a) is covered by the air-permeable outside air inflow suppressing member (40), the outside air can be taken into the inside of the exhaust gas sampling unit (10) from the sampling port (11) through the outside air inflow suppressing member (40) thereby allowing the airflow resistance of the outside air inflow suppressing member (40) to suppress the flow rate of the outside air flowing in as well. Therefore, it is possible to prevent leakage of the exhaust gas from the sampling port (11), which is caused by an increase in the outside air flow rate. Moreover, the leakage can be easily prevented even in a high speed range of the vehicle where leakage is likely to occur. For this reason, it is possible to prevent leakage at all vehicle speeds in the measurement range, and the entire amount of exhaust gas can be taken into the exhaust gas sampling unit (10).

In addition, while this is an open emission analysis, utilization of the outside air inflow suppressing member (40) makes it possible to reliably prevent leakage like in the case of the close emission analysis. Further, the advantages of not applying a load to the engine and not affecting the measurement in the open emission analysis can be enjoyed. As a result, it is possible to carry out a simple and reliable open emission analysis.

According to the invention of the second aspect, the outside air inflow suppressing member (40) suppresses the total inflow flow rate of the exhaust gas and the outside air flowing into the sampling port (11) to be less than the suction flow rate into the interior of the exhaust gas sampling unit (10). Therefore, reducing the total inflow flow rate to be always less than the suction flow rate prevents the leakage of exhaust gas caused by the total inflow flow rate exceeding the suction flow rate.

According to the invention of the third aspect, since the outside air inflow suppressing member (40) allows the exhaust gas to flow without interfering and the outside air to pass through while suppressing the speed of the air by air-flow resistance, only the inflow flow rate of the outside air can be suppressed. Therefore, accurate open emission analysis is enabled without affecting the flow rate of exhaust gas.

According to the invention of the fourth aspect, the outside air inflow gap located between the sampling port (11) of the exhaust gas sampling unit (10) and the periphery of the exhaust port (7a) is covered with the outside air inflow suppressing member (40) having air permeability. As a result, introducing the outside air into the sampling port (11) through the outside air inflow suppressing member (40) allows the flow rate of the outside air flowing in to be suppressed with the air-flow resistance. Therefore, it is possible to prevent leakage of the exhaust gas from the sampling port (11), which is caused by an increase in the outside air flow rate. Moreover, the leakage can be easily prevented even in the high speed range of the vehicle where the leakage is likely to occur. For this reason, it is possible to prevent leakage at all vehicle speeds in the measurement range, and the entire amount of exhaust gas can be taken into the exhaust gas sampling unit (10).

Moreover, since the outside air flow suppressing member (40) only covers the outside air inflow gap and has air permeability allowing it to take in the outside air, analysis may be carried out in the same way as in the conventional open emission analysis without the risk of causing an engine load which affects measurements as in the close emission analysis, thereby realizing a simple and highly reliable open emission analysis device.

According to the invention of the fifth aspect, since the outside air inflow suppressing member is the filter (40) and has a through hole (41) providing an exhaust gas passage (44). The filter (40) covers the sampling port (11) and the exhaust port (7a) faces the through hole (41) as well, and therefore the outside air inflow gap can be closed by the filter (40). With this configuration, an open emission analysis device having a simple structure and high reliability can be realized.

According to the invention of the sixth aspect, since the outside air inflow suppressing member (40) is disposed between the sampling port (11) and the end cap (6a), attachment of the outside air inflow suppressing member (40) is facilitated.

According to the invention of the seventh aspect, since the outside air inflow suppressing member (40) is held between the end cap (6a) and the curved portion (15) which is a turned-back edge portion of the sampling port (11A), the outside air inflow suppressing member (40) can be easily attached using the curved portion (15).

According to the invention of the eighth aspect, since the outside air inflow suppressing member (40) is made of a material that easily deforms its shape, even if other members such as a muffler and a tail pipe have irregular shapes and come into contact with the outside air inflow suppressing member (40), the outside air inflow suppressing member (40) can be easily deformed and can be brought into close contact with them.

Therefore, the connection becomes easy without requiring labor. In addition, the outside air inflow suppressing member (40) can be used commonly for a plurality of members having different shapes, and its versatility is enhanced since the emission boot and a special connecting jig are not used, thereby capable of reducing the number of stock members.

According to the invention of the ninth aspect, using a sponge material as the filter (40) allows air permeability thereof to be changed according to the roughness of the sponge material, and the adjustment of the outside air inflow rate by changing the air permeability is therefore facilitated. Further, because of the sponge material that is deformable in shape, the sponge material as the filter (40) can be provided airtightly between the collection port (11A) and the exhaust port (7a).

According to the invention of the tenth aspect, the roughness of the sponge material constituting the filter renders the total inflow flow rate of the exhaust gas and the outside air flowing into the sampling port (11) to be set less than the suction flow rate over the entire measurement range to be measured, and therefore it is possible to reliably prevent the exhaust gas from leaking out which has occurred in the high speed range or the like due to the total inflow flow rate of the exhaust gas and the outside air exceeding the suction flow rate. Also, the setting of the filter is facilitated because only the roughness of the sponge material needs to be selected for it.

BRIEF DESCRIPTION OF DRAWINGS

FIGS. 6A-6C are cross-sectional view of a sample filter used for setting characteristics, wherein FIG. 6A shows a butt type filter 45, FIG. 6B shows a push-in type filter 46, and FIG. 6C shows a fixed type filter with a fixed member.

FIG. 8 is a graph showing the attenuation characteristics (flow rate) of the filter.

FIG. 9 are graphs to detect leakage of exhaust gas, wherein

FIGS. 10A-10B are explanatory views of a leak prevention effect by the filter, wherein FIG. 10A shows leak prevention effect without the filter, and FIG. 10B shows the effect of suppressing the outside air inflow by using the filter.

FIGS. 12A-12D are views showing a variation of a member in contact with the filter, wherein FIG. 12A shows the end cap of the muffler having an inclined surface sloping downward toward the downstream side, FIG. 12B shows the end cap at a right angle relative to the filter, FIG. 12C shows the end cap having as an inclined surface and having a substantially triangular shape as viewed in the axial direction, and FIG. 12D shows a configuration provided with the end cap having the same irregular shape as that shown in FIG. 12C.

DETAILED DESCRIPTION

Hereinafter, a first exemplary embodiment of an open emission analysis method and device will be described with reference to FIGS. 1 to 10.

Figure 1:
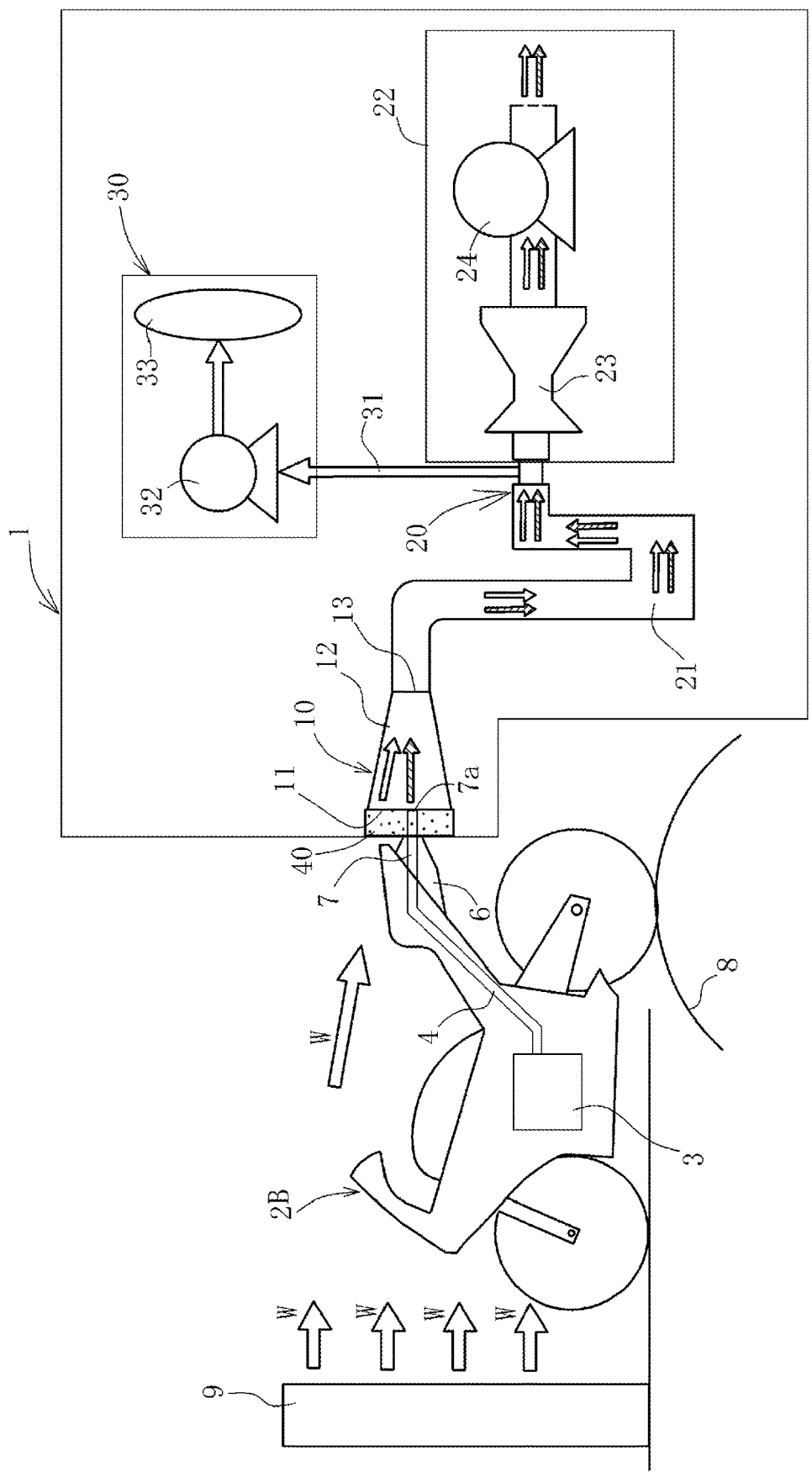
FIG. 1 is a diagram illustrating an open emission analysis system according to a first exemplary embodiment.

In FIG. 1, an open type exhaust gas analysis system (open emission analysis system) 1 of the present exemplary embodiment includes an open type exhaust gas sampling unit 10 for collecting exhaust gas discharged from the rear portion of a motorcycle 2 together with ambient outside air, a quantitative flow path 20 that is connected to the exhaust gas sampling unit 10 and through which the exhaust gas and the outside air sampled from the exhaust gas sampling unit 10 mix and flow, and a concentration analyzing unit 30 for collecting some of the mixed gas in the quantitative flow path 20 and measuring the concentration.

The exhaust gas discharged from an engine 3 of the motorcycle 2 is sent to the rear of the vehicle through an exhaust pipe 4 and discharged to the rear via a muffler 6 and a tail pipe 7 projecting rearward from the rear end portion of the vehicle. The exhaust port 7a is located at the rear end portion of the tail pipe 7, etc. However, the tail pipe 7 is not necessarily provided and may be omitted. In this case, the rear end portion of the muffler 6 or the like serves as the exhaust port. Furthermore, the rear end portion of the exhaust pipe 4 may protrude from the rear end portion of the muffler, and this protruding portion may be used as the exhaust port.

The rear wheel of the motorcycle 2 is placed on a chassis dynamometer 8, and the rotation of the engine 3 can be changed in a predetermined running mode (emission mode). A blower fan 9 is disposed in front of the vehicle, and traveling wind W that is proportional to the speed of the vehicle is blown toward the vehicle.

This traveling wind W flows to the rear of the vehicle and is taken into the exhaust gas sampling unit 10 together with the exhaust gas.

The exhaust gas sampling unit 10 is provided substantially opposite to the exhaust port 7a and has a sampling port 11 which is larger than the exhaust port 7a. Between the exhaust port 7a and the sampling port 11, an outside air inflow gap (details will be described later) is provided.

In addition to taking in the exhaust gas discharged from the exhaust port 7a, the exhaust gas sampling unit 10 also takes in the running wind and the atmosphere (hereinafter referred to as outside air) around the exhaust port 7a from the outside air inflow gap.

In the quantitative flow path 20, a mixing section 21 for stirring and mixing the exhaust gas and the outside air, and a constant flow rate mechanism 22 for keeping the flow rate of the fluid flowing through the quantitative flow path 20 constant are provided in this order from the upstream side.

The mixing section 21 removes dust by a cyclone or the like, stirs and mixes the exhaust gas and the outside air, and generates a mixed gas obtained by diluting the exhaust gas with traveling wind. However, the mixing section 21 may be omitted.

The constant flow rate mechanism 22 regulates the flow rate so that the total flow rate of the mixed gas becomes constant, and includes a venturi 23 composed of a critical flow rate venturi, and a suction blower 24 connected downstream of the venturi 23. The suction blower 24 is an example of a suction means for sucking the gas inside the quantitative flow path 20 and the exhaust gas sampling unit 10.

The mixed gas in the quantitative flow path 20 is sucked by the suction blower 24 to make the differential pressure between the upstream side and the downstream side of the venturi 23 equal to or higher than a predetermined value to thereby keep the total flow rate of the mixed gas flowing through the quantitative flow path 20 constant. The mixed gas sucked by the suction blower 24 is discharged to the outside.

It is to be noted that the constant flow rate mechanism is not limited to the above-described configuration and various well-known devices such as a configuration including a critical orifice and a suction pump can be used. In addition, instead of the constant flow rate mechanism, a variable flow rate control mechanism may be used.

A sampling line 31 for collecting a portion of the mixed gas flowing through the quantitative flow path 20 is connected between the mixing section 21 and the constant flow rate mechanism 22 in the quantitative flow path 20. An analyzer 33 for analyzing the mixed gas sampled from the sampling line 31 via the suction pump 32 is connected to the sampling line 31.

The analyzer 33 is, for example, a sampling bag for collecting the sampled mixed gas. The concentration of a predetermined component contained in the mixed gas collected in this collection bag is analyzed by a known analyzer such as NDIR, for example.

Figure 2:
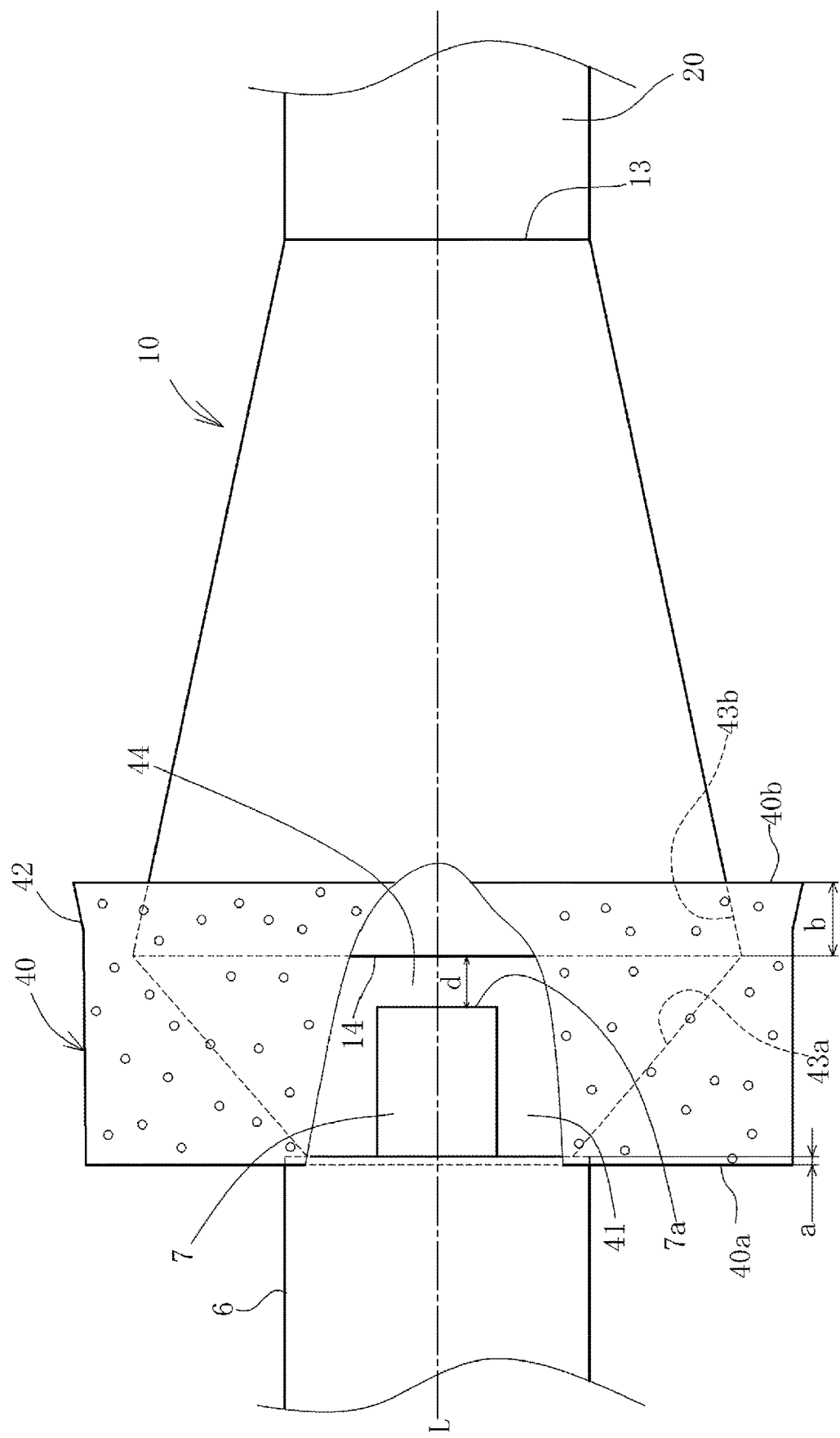
FIG. 2 is a partial cutaway side view of a part mainly including an exhaust gas sampling unit of the above system.
Figure 3:
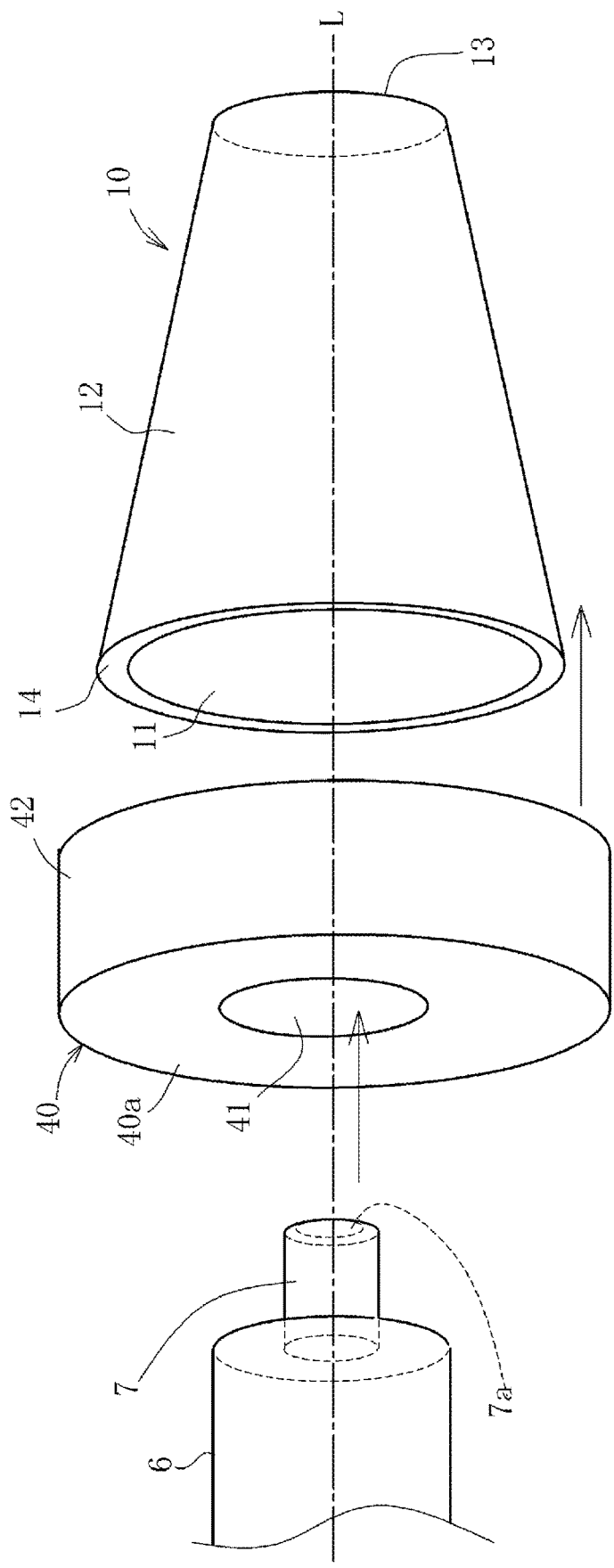
FIG. 3 is an exploded perspective view of a part mainly including the exhaust gas sampling unit in FIG. 2.
Figure 4:
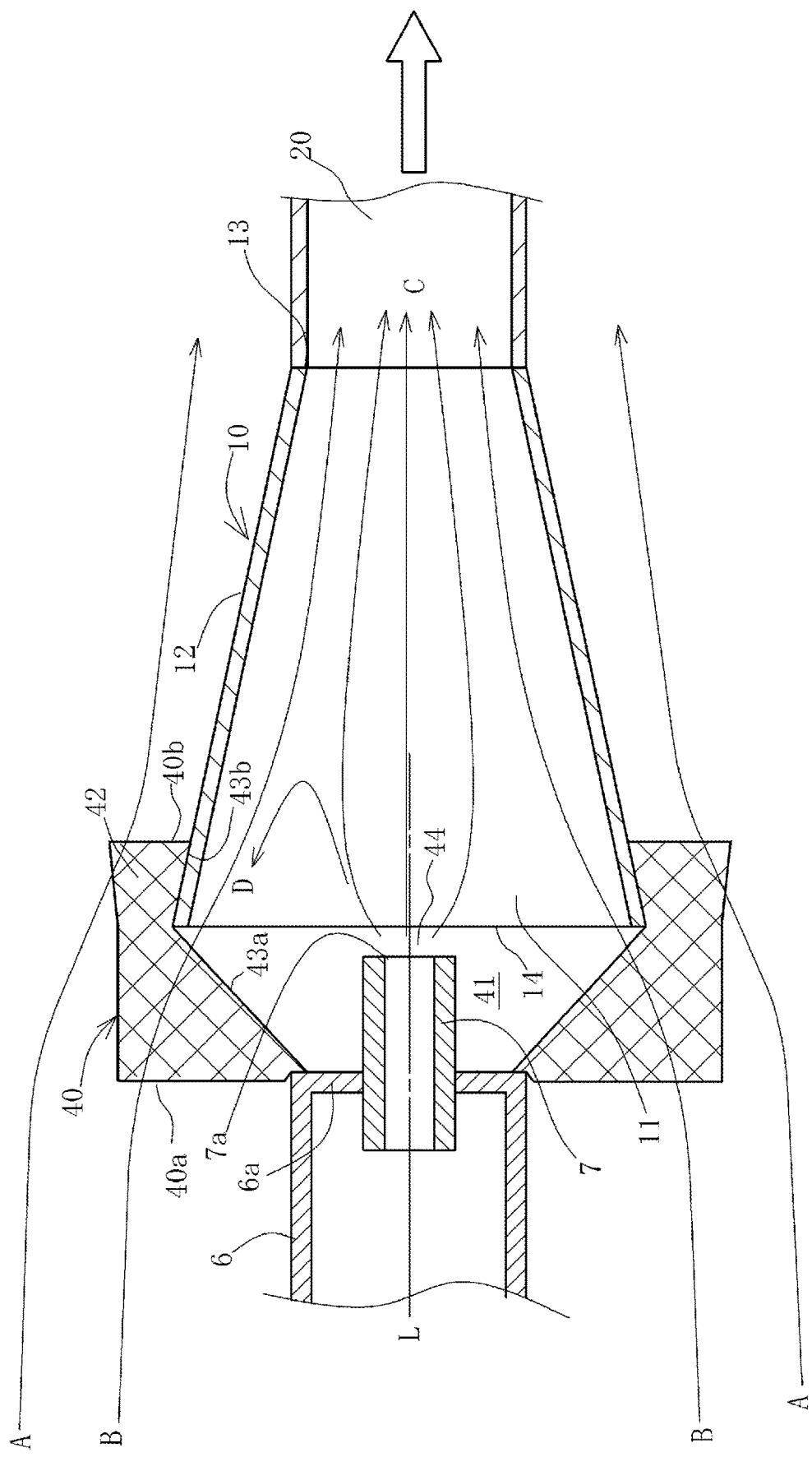
FIG. 4 is an axial sectional view of the part shown in FIG. 2.

Hereinafter, a structure of the exhaust gas sampling unit 10 and the vicinity thereof will be described in detail with reference to FIGS. 2 to 5. FIG. 2 is a diagram illustrating a side view of the exhaust gas sampling unit 10 together with the front and rear members. FIG. 3 is an exploded perspective view showing the exhaust gas sampling unit 10 and parts connected thereto. FIG. 4 is a sectional view taken along the axial direction of FIG. 2.

As shown in these figures, the exhaust gas sampling unit 10 is in the form of a cone having a tubular shape (a circular tube shape having a hollow truncated conical shape), opens with an enlarged diameter on the upstream side, and when viewed from the side, has a substantially truncated cone shape gradually decreasing in diameter from the upstream side to the downstream side and the side surface thereof is a tapered surface 12. The upstream end portion is the circular sampling port 11 which is a large diameter opening.

An upstream side end portion of the quantitative flow path 20 is connected to an opening 13 on the downstream side of the exhaust gas sampling unit 10. The passage cross sectional area of the exhaust gas sampling unit 10 gradually decreases from the upstream side to the downstream side.

Note that the shape of the opening of the sampling port 11 and the opening 13 on the downstream side and the passage cross sectional shape of the exhaust gas sampling unit 10 are not limited to a circular shape, but that a polygonal shape such as a rectangular or triangular shape or an ellipse shape may be used.

In this embodiment, the exhaust port 7a is disposed on a central axis line L of the exhaust gas sampling unit 10 at a certain distance (denoted by "d" in FIG. 2) spaced apart upstream from the sampling port 11. However, the exhaust port 7a may be positioned anywhere and is not limited thereto but may be inserted into the exhaust gas sampling unit 10 through the sampling port 11, or may be disposed so as to overlap an opening edge portion 14 (see FIG. 3) of the sampling port 11 in the side view (FIG. 2).

As shown in FIG. 4, the sampling port 11 is covered by the filter 40. The opening edge portion 14 of the sampling port 11 is a cut-off end portion on the upstream side of the tapered portion 12, and an outer insertion portion 42 of the filter 40 is externally fitted to the periphery of the opening edge portion 14. The filter 40 in the present exemplary embodiment is made of a sponge material having air permeability and elasticity, such as polyurethane foam, and is an example of the outside air inflow suppressing member in the present application and is a member for restricting the flow rate of outside air taken in from the sampling port 11 into the inside of the exhaust gas sampling unit 10 by air-flow resistance. The magnitude of the air-flow resistance is appropriately set.

The filter 40 is a tubular member having a ring shape that is substantially donut-shaped, and centrally has a through hole 41 of a size that allows the exhaust port 7a to enter. The through hole 41 includes an internal space on the downstream side from the exhaust port 7a that serves as an exhaust gas passage 44, and through which the exhaust gas discharged from the exhaust port 7a flows toward the sampling port 11.

The filter 40 has two ends in the axial direction: one on the muffler 6 side is defined with an upstream surface 40a, and the other on the sampling port 11 is defined with a downstream surface 40b. Taking into consideration the various shapes and sizes of the exhaust port 7a, the tail pipe 7, and the muffler 6, the through hole 41 which is open in the upstream surface 40a is configured to a versatile size, for example, comparatively small.

The through hole 41 includes an internal surface the inclination of which differs between the upstream side and the downstream side. The internal surface of the upstream side portion forms a first inclined surface 43a that widens from the opening of the upstream surface 40a to the downstream side. The downstream side portion is a portion formed in the outer insertion portion 42, and the inclination of the inner surface is continuous with the first inclined surface 43a and reversely inclined to form a second inclined surface 43b that changes so as to narrow the through hole 41 toward the downstream side. The inclination of the second inclined surface 43b is substantially parallel to the inclination of the tapered surface 12 and the hole (downstream portion of the through hole 41) defined by the second inclined surface 43b has an inner diameter that is slightly smaller than the outer diameter of the tapered surface 12 in the vicinity of the sampling port 11.

Therefore, when the outer insertion portion 42 of the filter 40 is fitted to the portion in the vicinity of the sampling port 11 of the exhaust gas sampling unit 10, and the outer peripheral part of the portion in the vicinity of the sampling port 11 is inserted into the downstream side portion of the through hole 41 that is defined by the second inclined surface 43b, because the filter 40 is made of a deformable material that is very elastic and relatively soft, the portion near the sampling port 11 can be inserted while the outer insertion portion 42 deforms and expands outward.

As a result, without requiring any special jig or fixing member, the filter 40 is externally inserted and closely fixed to the exhaust gas sampling unit 10 in a state where the outer peripheral surface of the portion near the sampling port 11 of the exhaust gas sampling unit 10 and the second inclined surface 43b are in close contact with each other and closely covering the sampling port 11. The outer insertion portion 42 of the filter 40 includes a portion of a length "b" (see FIG. 2) to be fitted to the outer peripheral portion of the exhaust gas sampling unit 10, and the length "b" can be arbitrarily set so that the filter 40 is stably fixed thereon when externally inserted.

Note that the degree of the inclination of the second inclined surface 43b in the downstream side portion of the through hole 41 is arbitrary. Further, instead of a tapered hole provided with the second inclined surface 43b, the downstream side portion of the through hole 41 may be a straight hole whose inner diameter is smaller than the outer diameter of the sampling port 11 and whose inner peripheral surface is substantially parallel to the central axis L.

The tail pipe 7 provided with the exhaust port 7a protrudes rearward from the end cap 6a which seals the rear end of the muffler 6. The outer diameter of the tail pipe 7 is smaller than and the outer diameter of the end cap 6a, and is larger than the inner diameter of the opening of the through hole 41 in the upstream surface 40a. With respect to the filter 40 which is externally inserted and fixed to the vicinity of the sampling port 11, the exhaust port 7a is inserted from the upstream surface 40a side into the through hole 41.

Then, upon pressing the end cap 6a of the muffler 6 against the filter 40, the opening peripheral portion of the through hole 41 in the upstream surface 40a of the filter 40 is pushed in by the end cap 6a.

At this time, the filter 40 elastically deforms so as to generate a biting such as a dimension "a" (refer to FIG. 2) against the general surface of the upstream surface 40a (the surface not pressed by the end cap 6a) so as to come in close contact with the end cap 6a, thereby enabling the end cap 6a to tightly seal the opening of the through hole 41.

As a result, the filter 40 is in a state of being sandwiched between the opening edge portion 14 of the sampling port 11 and the end cap 6a. In this state, the exhaust port 7a is connected to the sampling port 11 via the filter 40, and the outside air inflow gap located between the exhaust port 7a and the sampling port 11 is closed by the filter 40. However, since the filter 40 has air permeability, it is possible to take in outside air composed of traveling wind etc. into the sampling port 11 from around the muffler 6 as indicated by the arrow B in FIG. 4.

It is to be noted that the fixing of the filter 40 is not only through fitting by externally inserting the filter 40 to the periphery of the sampling port 11 but that other fixing methods are possible. For example, a fixing member such as a resin band having one end attached to the filter 40 may be provided, and the other end of the fixing member may be fixed to the outer peripheral surface of the exhaust gas sampling unit 10 by an appropriate means such as locking. However, regardless of this example, various fixing means can be adopted.

In a state where the exhaust port 7a and the sampling port 11 are connected via the filter 40 shown in FIG. 4, the exhaust gas discharged from the exhaust port 7a passes through the exhaust gas passage 44 as indicated by the arrow C and enters the sampling port 11 without any resistance. Thereafter, the exhaust gas is mixed with the outside air indicated by the arrow B on the downstream side of the sampling port 11, and becomes a mixed gas flowing from the exhaust gas sampling unit 10 to the quantitative flow path 20.

Figure 5:
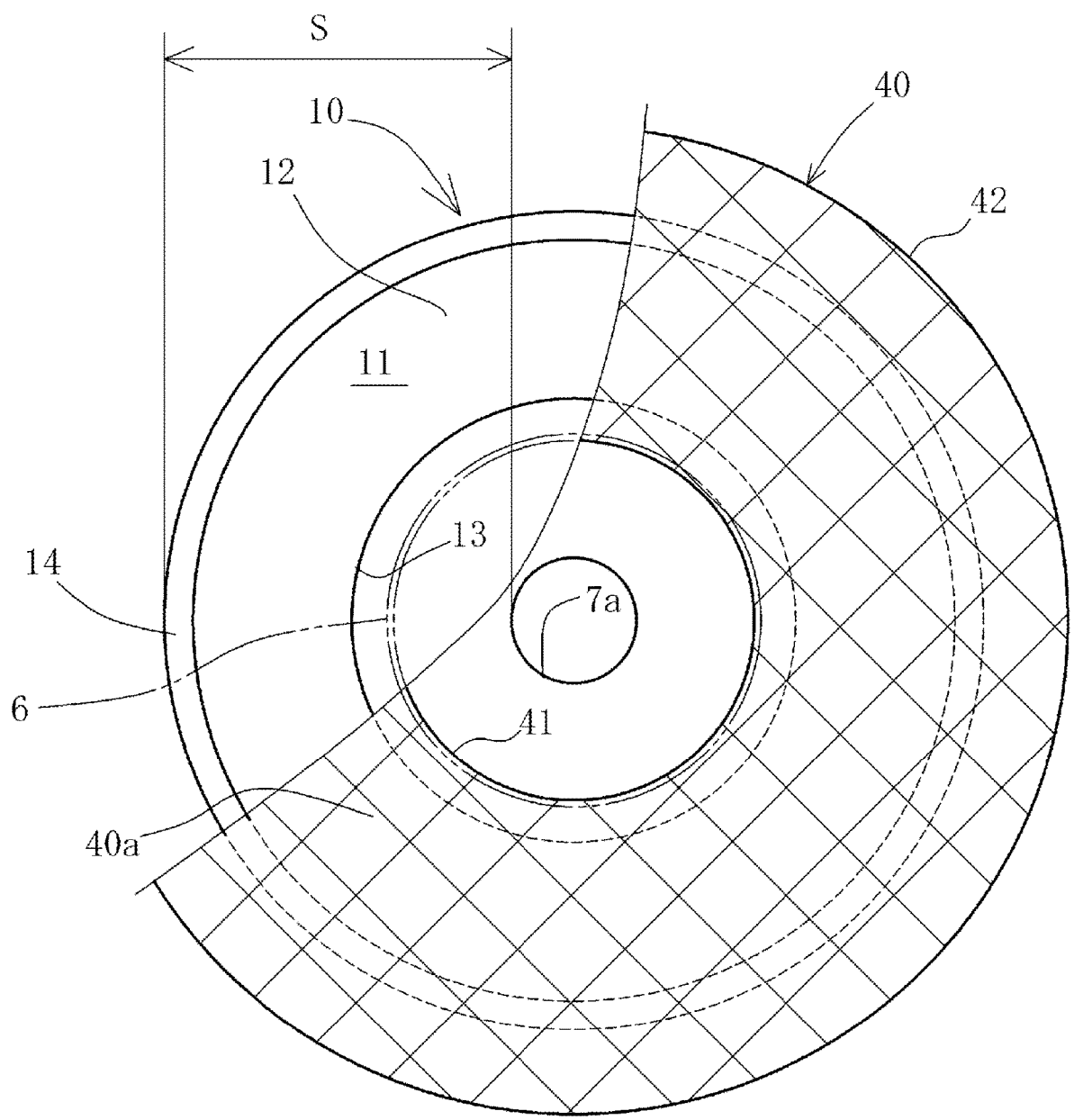
FIG. 5 is an axial directional view of a part mainly including the exhaust gas sampling unit in FIG. 2.

FIG. 5 is an axial directional view (front view) illustrating the exhaust gas sampling unit 10 and the filter 40 from the upstream side along the central axis line L (FIG. 4) of the exhaust gas sampling unit 10, and also illustrated are the tail pipe 7 and the arrangement of the exhaust port 7a. In the present exemplary embodiment, for the sake of convenience, the exhaust gas sampling unit 10, the filter 40, the end cap 6a of the muffler 6, the tail pipe 7 and the exhaust port 7a thereof are all circular in shape in the axial direction. However, each shape is not limited to a circular shape, and various shapes are possible as will be described later.

As shown in this figure, the opening edges of the sampling port 11 and that of the opening 13 on the downstream side are concentric. Furthermore, if the tail pipe 7 is also cylindrical, then preferably it is disposed coaxially with the exhaust gas sampling unit 10, and the circular exhaust port 7a is also disposed substantially concentrically with respect to the sampling port 11 and the opening 13 on the downstream side.

A concentric gap exist at intervals of a distance S between the exhaust port 7a and the opening edge portion 14 of the sampling port 11. The gap in this axial directional view is referred to as the outside air inflow gap. The outside air around the exhaust port 7a flows through the outside air inflow gap into the sampling port 11.

Further, in this embodiment, the outside air inflow gap is concentric when viewed in the axial direction, but various shapes can be adopted according to the shape of the exhaust port 7a and the sampling port 11.

The filter 40 has an outer diameter larger than the outer diameter of the opening edge portion 14 of the sampling port 11, and therefore can cover the opening edge portion. Further, the diameter of the exhaust port 7a is smaller than the diameter of the opening 13 on the downstream side.

Figure 6A:
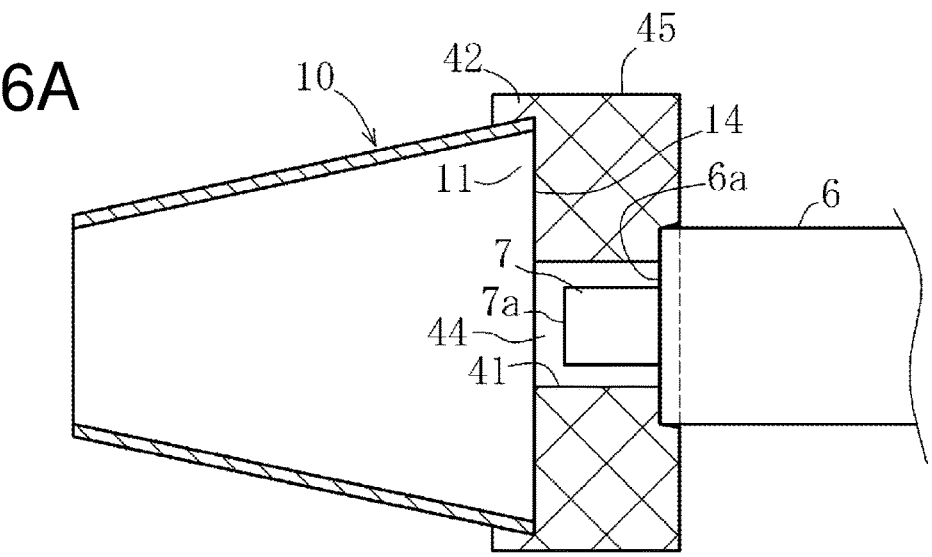
Figure 6B:
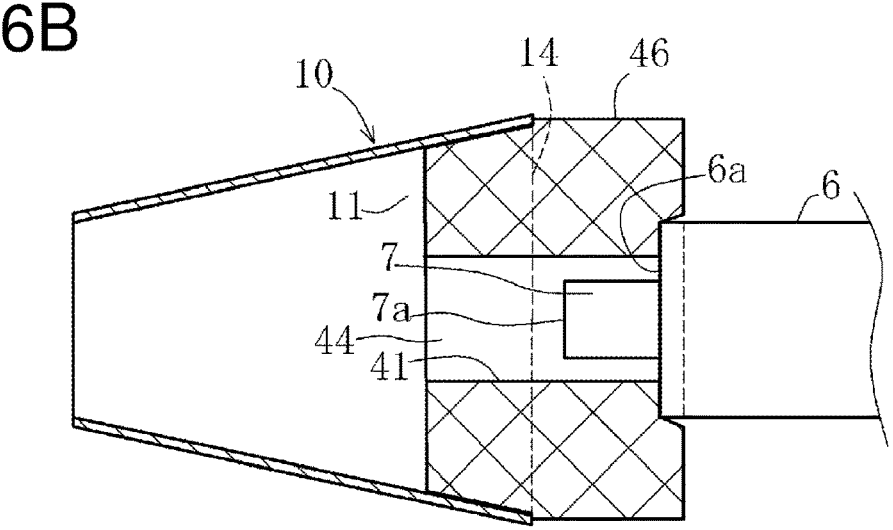
Figure 6C:
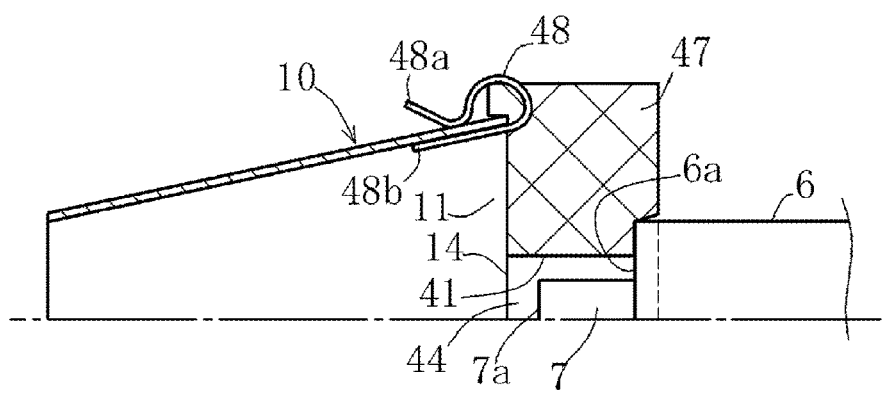

Next, various fixing types of the filter 40 with respect to the exhaust gas sampling unit 10 will be described. Shown in FIG. 6A is a butt type filter 45, in FIG. 6B is a push-in type filter 46, and in FIG. 6C is a fixed type filter 47 with a fixed member. These types of filters are made of the same sponge material as the one described above, and have air permeability and moderate elasticity. Moreover, the use of these various filters (45, 46, and 47) are intended for explaining the differences concerning these fixed types, and the filter 40 described so far and hereafter includes these various filters (45, 46, and 47).

In FIG. 6A, the butt type filter 45 is sandwiched between the opening edge portion 14 and the end cap 6a in a state in which the downstream surface of the butt type filter 45 is abutted against the opening edge portion 14 of the sampling port 11 and the upstream surface is abutted against the end cap 6a. The butt type filter 45 has a thickness that is set so that the interval between the sampling port 11 and the exhaust port 7a becomes appropriate.

Note that the outer peripheral portion on the downstream side of the butt type filter 45 may be provided with an outer insertion portion 42 that can be externally fitted to the periphery of the sampling port 11. This configuration is similar to that of Fig, 4 with the provision of the outer insertion portion 42. However, in this example, the through hole 41 is a straight hole.

In FIG. 6B, the push-in type filter 46 is thicker (longer in the axial direction) than the butt type filter 45, and the downstream side portion thereof is pushed into the inside from the sampling port 11. As a result, the interval between the sampling port 11 and the exhaust port 7a is made appropriate, and since the exhaust gas sampling unit 10 has a tapered shape, by only pushing in the fine filter 46, the shape thereof easily deforms as the frictional force is increased due to the amount of deformation, which leads to the fine filter 46 being reliably positioned and fixed. Therefore, the filter can be mounted compactly inward without extending to the outside of the sampling port 11.

Note that the side surface of the push-in type filter 46 may be partially inclined in a tapered shape.

FIG. 6C shows a fixed type filter 47 with a fixing member. In this example, a butt type filter having almost no outer insertion portion is used and fixed to the periphery of the sampling port 11 by a pin 48 as the fixing member. One end 48a of the pin 48 is inserted into the outer peripheral surface side around the sampling port 11 and another end 48b thereof penetrates the filter to be inserted into the inner peripheral surface side around the sampling port 11. The inner and outer circumferences of the sampling port 11 is clamped by both end portions 48a and 48b.

The filter is made of a sponge material and therefore facilitates the insertion of the pin. However, a hole for the insertion of the pin may be provided in advance as desired.

A plurality of these pins 48 are preferably provided in the circumferential direction of the sampling port 11. This configuration allows the filter to be more reliably fixed.

It is to be noted that this fixed type can also be used in combination with the push-in type filter 46. In addition, various fixing members other than that shown in the drawings may be used.

Figure 7:
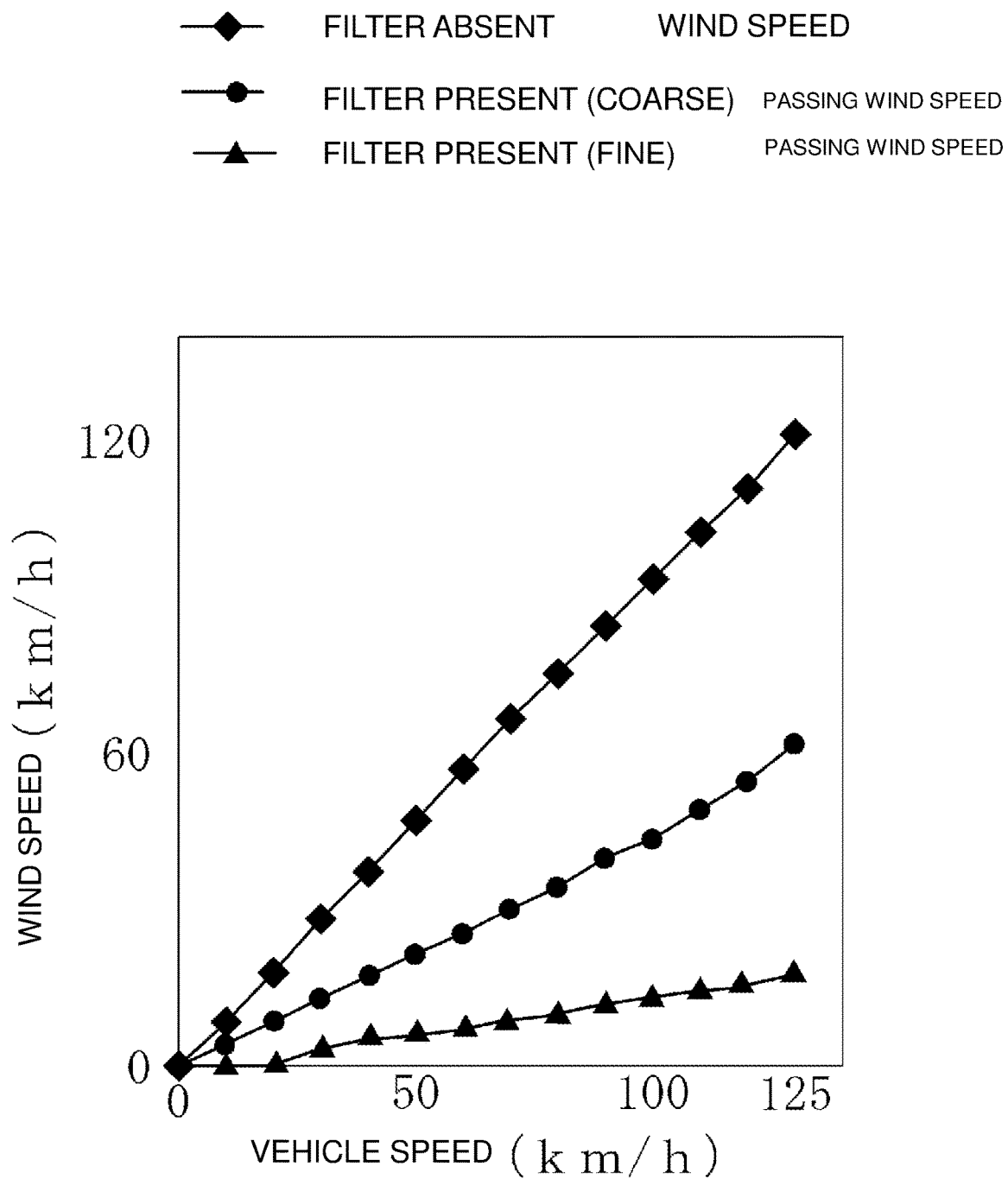
FIG. 7 is a graph showing the attenuation characteristics (wind speed) of the filter.

FIGS. 7 to 10 are graphs for explaining the suppression of outside air inflow by means of the filter 40. First, FIG. 7 shows the attenuation characteristic of the wind speed as the characteristic related to the air permeability of the filter of the present application. In order to set this characteristic, two types of filters having different air permeability are prepared as samples, that is, a coarse filter and a fine filter are prepared.

The coarse filter has a higher air permeability and a thinner wall thickness than the fine filter. Conversely, the fine filter has a lower air permeability and a thicker wall thickness than the coarse filter, and air permeability and wall thickness thereof are set under optimal conditions. These filters are made of the same sponge as those described above and have air permeability and moderate elasticity.

In the graph illustrated in FIG. 7, the exhaust gas sampling unit 10 has, for example, a sampling port 11 of a 150φ that is disposed on the downstream side of the blowing fan. Wind speed was measured at the same position in the exhaust gas sampling unit 10 for cases including: one case where a filter is not interposed between the blowing fan and the sampling port 11; and the other a case in which the above described two kinds of filters are interposed. The horizontal axis indicates the vehicle speed and the vertical axis indicates the measured wind speed. It should be noted that the size of the diameter of the sampling port 11 is an example and various changes may be made according to specifications.

In the case where the filter is not interposed, the wind speed of the air blown by the blower fan is shown as is, and rises linearly to the right as the vehicle speed increases.

When a coarse filter is used, the speed of the traveling wind speed is attenuated by the air-flow resistance (filter resistance), and the inclination of the straight line is less steep than in the case without the filter.

In the case of the fine filter, since the air-flow resistance (filter resistance) is further increased, the wind speed of the passing wind is further attenuated and the inclination of the straight line is therefore milder.

In setting the filter, first, it is necessary to satisfy this attenuation characteristic. Both of these two types of filters are qualified to attenuate the characteristic of the wind speed, and furthermore, each filter is set to have the following flow rate characteristic.

FIG. 8 is a graph relating to the setting of the flow rate characteristic, and shows the relationship between the total inflow flow rate of the exhaust gas and the outside air flow rate taken into the exhaust gas sampling unit 10 and the vehicle speed. Illustrated in this graph is the change in the vehicle speed against the inflow flow rate for three kinds of filters including the coarse filter and the fine filter described in the above FIG. 7 as well as the intermediate medium filter.

Here, the fine filter is set as filter A, the medium filter as filter B, and the coarse filter as filter C. Each filter is in the range satisfying the attenuation characteristic of FIG. 7, and the roughness of the sponge material that affects the air permeability is set in the order of fine to coarse, that is, filter A<filter B<filter C.

Further, the inflow flow rate of exhaust gas is also independently shown in the graph of the figure.

Note that the horizontal axis represents the vehicle speed (km/h) in the measurement range, and the vertical axis represents the inflow flow rate of the gas flowing into the exhaust gas sampling unit 10. The suction flow rate by the suction blower 24 is fixed at, for example, 4.5 m$^3$/min at all vehicle speeds. However, it is possible to arbitrarily set the suction flow rate.

In this graph, without a filter, the inflow flow rate exceeds the suction flow rate at the vehicle speed of around 115 km/h, indicating that in the high speed range from 115 km/h up to the upper speed limit (125 km/h) in the measurement of this example, as will be described later, there is occurrence of exhaust gas leakage, resulting in measurement failure.

On the other hand, when there is a filter, in the case for each of the filter A (fine material) and the filter B (medium material), the inflow flow rate does not exceed the suction flow rate even in the high speed range where the vehicle speed is up to the upper speed limit (125 km/h) including the above measurement failure range. In the entire measurement range (0 to 125 km/h), the inflow flow rate is less than the suction flow rate.

However, in the case of the filter C (coarse material), the inflow flow rate exceeds the suction flow rate at the vehicle speed of about 120 km/h near the upper speed limit of measurement (125 km/h). Therefore, the filter C (rough material) is more capable of suppressing the inflow flow rate to be less than the suction flow rate in the high speed range than in the case without the filter, but a small range near the upper speed limit (125 km/h) falls within the measurement failure range.

As a result, both the filter A and the filter B, in which the inflow flow rate does not exceed the suction flow rate over the entire range of the vehicle speed in the measurement range, are determined to have qualified characteristics, whereas the filter C is determined as unsuitable. Therefore, it is possible to appropriately construct and use a filter having optimum characteristics within the range of a fine to medium material. In other words, the flow rate characteristic of the filter is set such that the inflow flow rate does not exceed the suction flow rate over the entire measurement range.

Since the exhaust gas does not pass through each filter, the flow rate of the outside air passing through each filter is a flow rate obtained by excluding the flow rate of the exhaust gas from the graph shown in the figure (denoted as "outside air" on the right vertical axis side of the graph), and the airflow characteristic of each filter is set to this flow rate.

Figure 9A:
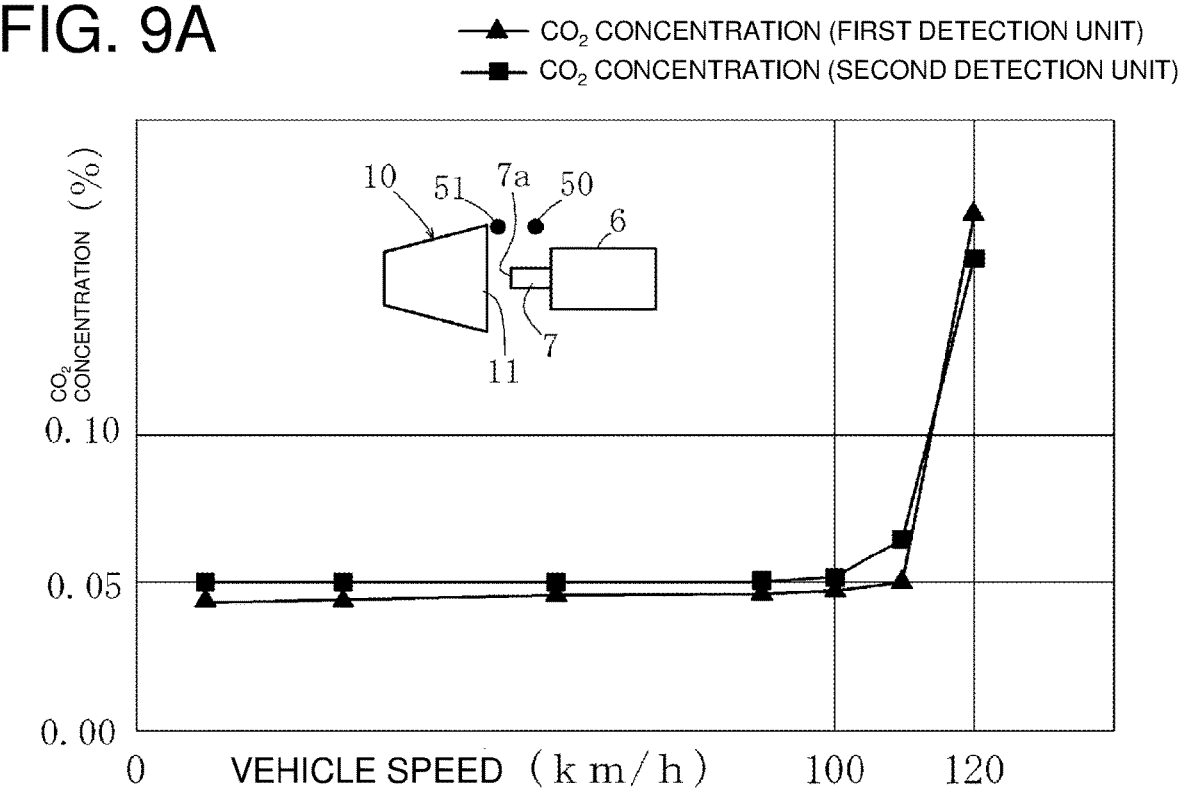
FIG. 9A shows a state without a filter.
Figure 9B:
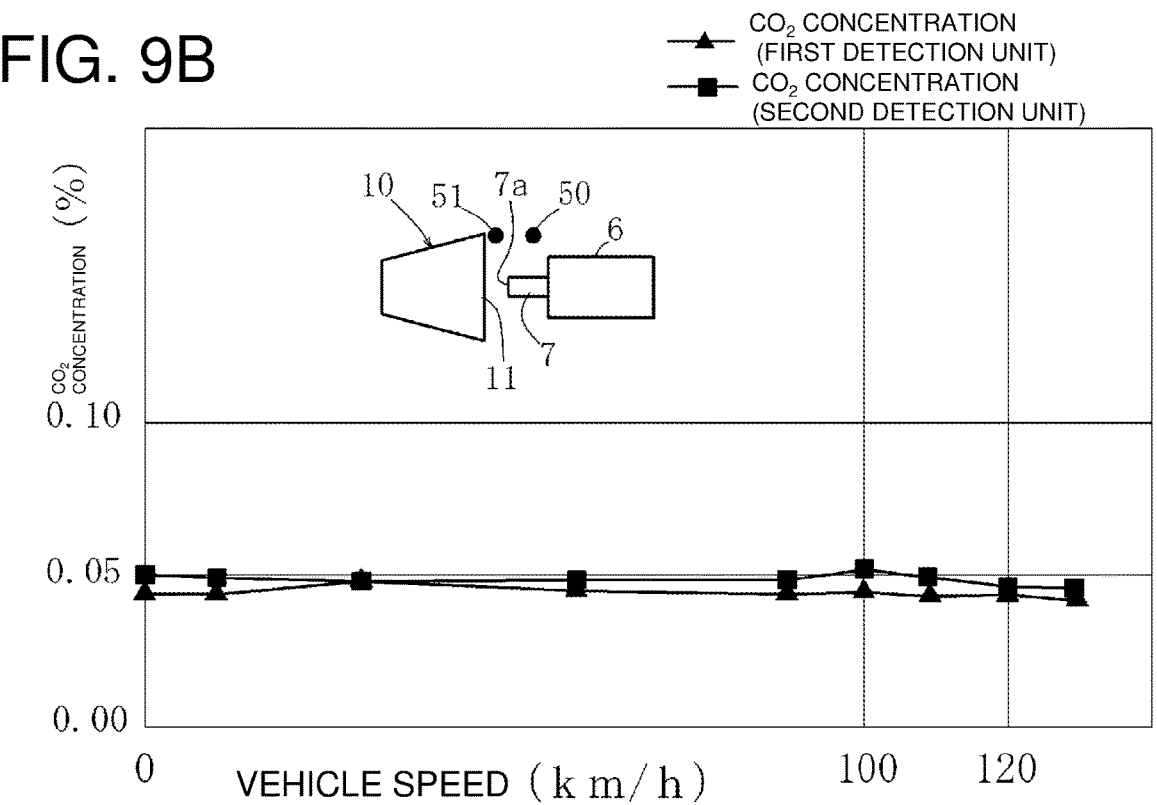
FIG. 9B shows a state with a filter.

FIGS. 9A-9B are graphs showing the comparative verification of the presence or absence of exhaust gas leakage due to the presence or absence of a filter, where FIG. 9A shows a state without a filter and FIG. 9B shows a state with a filter. The following filters may be either a medium filter or a fine filter, or may be other filters provided with the setting conditions as described above. Hereinafter, it is assumed that a medium filter is used.

In each of the graphs in FIG. 9A and FIG. 9B, the concentration (%) of $CO_2$ is indicated on the vertical axis and the vehicle speed (km/h) on the horizontal axis.

The concentration of $CO_2$ is measured by measuring the concentration of $CO_2$, which is an example of a specific component in the leaking exhaust gas, by a known method. The component to be subjected to concentration measurement is but not limited to $CO_2$ and may be other components.

As shown by the schematic diagram in the figure, measurement is carried out at two locations by means of a first detection unit 50, which is located upstream of the sampling port 11 and upstream around the exhaust port 7a, and a second detection unit 51 located in the vicinity of the sampling port 11 on the downstream side thereof.

When the engine 3 of a vehicle is operated in a predetermined emission mode to change the vehicle speed, there is a sharp rise in the concentration of $CO_2$ if there is a leak. Assuming that the concentration (%) of $CO_2$ is 0.1 set as the threshold value, if concentration is less than or equal to this threshold value, it indicates that there is no leakage; and if concentration exceeds the threshold value, it indicates that leakage has occurred.

As shown in FIG. 9A, when a filter is not provided and the vehicle speed is in the high speed range, exhaust gas leakage begins to occur when the vehicle speed exceeds 100 km/h. At this time, since the exhaust gas leaks from the vicinity of the sampling port 11 towards the second detection unit 51, the concentration of the specific component detected by the second detection unit 51 sharply rises, thereby detecting a leak.

At this time, the arrival of the exhaust gas to the first detection unit 50 on the upstream side is delayed, and therefore the concentration detection carried out by the first detection unit 50 will be delayed. As a result, when the vehicle speed reaches around 120 km/h, the concentration exceeds the threshold value in both the first detection unit 50 and the second detection unit 51, thereby detecting the occurrence of leakage.

On the other hand, as shown in FIG. 9B, in the case of using a filter in which the speed of the vehicle is high and exceeding the 120 km/h, even reaching the upper speed limit of measurement, the concentration in any of the first detection unit 50 and the second detection unit 51 remains below the threshold value, indicating that no leakage has occurred. Therefore, it can be seen that no leakage occurs in the total measurement range when a filter is used.

Figure 10A:
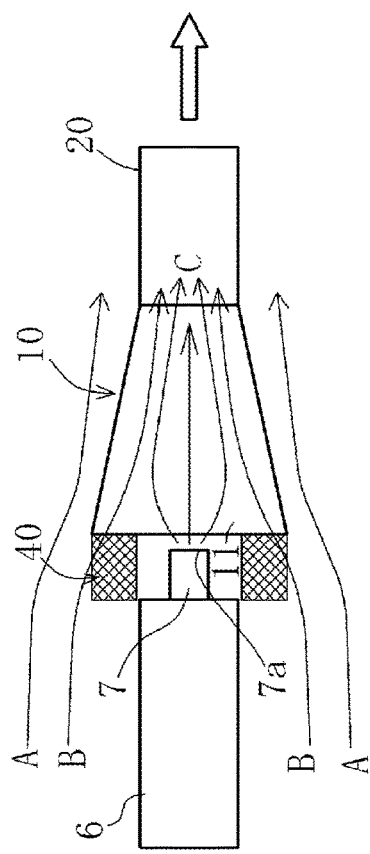
Figure 10B:
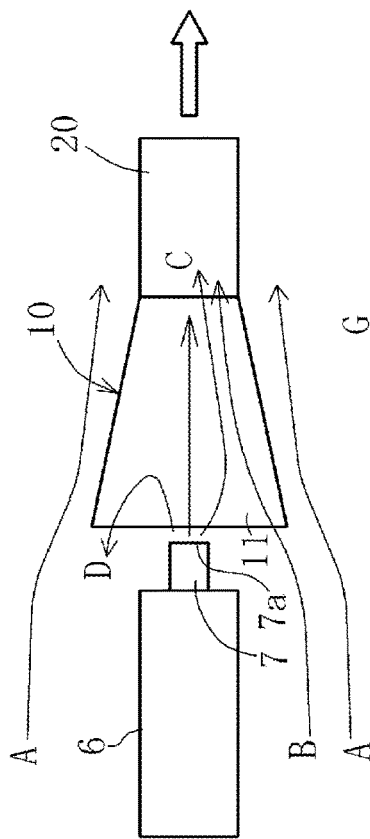

FIG. 10B shows the effect of suppressing the outside air inflow by using the filter 40 set in this way. In this figure, the inflow flow rate of the outside air to be taken into the interior of the exhaust gas sampling unit 10 from the sampling port 11 is suppressed and is less than by the suppression amount H as compared with the inflow flow rate of the state without the filter shown in FIG. 10A. Since the inflow flow rate of the exhaust gas is the same as that in FIG. 10A, as a result, the inflow total flow rate of the outside air and the exhaust gas is reduced by the suppression amount H and becomes less than the suction flow rate. As a result, the leakage of the exhaust gas is prevented.

Moreover, since this state appears in the vicinity of the maximum vehicle speed in FIGS. 8 and 9B, eventually, the total inflow flow rate of the outside air and the exhaust gas is set lower than the suction flow rate at all vehicle speeds in the measurement range. Therefore, it is possible to prevent leakage of the exhaust gas caused by the total inflow flow rate of the outside air and the exhaust gas exceeding the suction flow rate.

Next, an implementation of the open emission analysis and its operation in the present exemplary embodiment constituted in this way will be described.

First, as shown in FIGS. 2 and 3, for example, the filter 40 is attached to the sampling port 11 in advance, the exhaust port 7a of the tail pipe 7 is inserted into the exhaust gas passage 41, the end cap 6a of the muffler 6 is brought close contact into the filter 40, and the periphery of the exhaust port 7a is tightly surrounded by the filter 40, thereby closing the outside air inflow gap formed between the exhaust port 7a and the sampling port 11 with the filter 40.

In this state, the suction blower 24 of the exhaust gas analysis system 1 is started. At the same time, the engine 3 is started and operated in a predetermined emission mode. Corresponding to the operation of the engine 3, the blower fan 9 blows the traveling wind W corresponding to the vehicle speed toward the vehicle.

Then, the exhaust gas discharged from the exhaust port 7a and the outside air around the exhaust port 7a are sucked into the inside of the exhaust gas sampling unit 10 from the sampling port 11. Furthermore, the exhaust gas and the outside air are mixed to form a mixed gas and introduced to the quantitative flow path 20.

The mixed gas in the quantitative flow path 20 is sampled by the sampling line 31, and the concentration thereof is measured for each specific component by the analyzer 33 of the concentration analyzing unit 30.

At this time, the exhaust port 7a and the sampling port 11 are connected via the filter 40 and the outside air inflow gap between the exhaust port 7a and the sampling port 11 is closed by the filter 40. Therefore, the presence of the filter 40 itself serves as a blocking member for directly preventing the leakage of the exhaust gas, which makes it possible to prevent a portion of the exhaust gas from leaking out through this gap.

In addition, the filter 40 has air permeability and it allows the outside air to pass through while suppressing the inflow flow rate of the outside air by the air-flow resistance. Therefore, the total inflow flow rate including the exhaust gas is set, as shown in FIG. 10B, less than the suction flow rate at all vehicle speeds in the measurement range.

For this reason, it is possible to prevent the exhaust gas from leaking even if the vehicle speed becomes high. As a result, it is possible to take in the total amount of exhaust gas and perform measurement at all vehicle speeds in the measurement range, enabling accurate open emission analysis.

In addition, while this is an open emission analysis, using the filter 40 makes it possible to reliably prevent leakage like in the case of the close emission analysis. Further, the advantages of the open emission analysis which does not apply a load to the engine and affect the measurement can be enjoyed.

Additionally, since the filter 40 does not interfere with the exhaust gas as it passes but only suppresses the wind speed of the outside air by air-flow resistance while allowing it to pass, the filter 40 does not affect the inflow flow rate of the exhaust gas, thereby enabling accurate open emission analysis.

Moreover, since the filter 40 has air permeability and is capable of taking in outside air, analysis can be carried out in the same way as in the conventional open emission analysis without the risk of causing an engine load which affects measurements as in the close emission analysis.

As a result, a simple and highly reliable open emission analysis is achieved.

Further, the filter 40 merely covers the outside air inflow gap, allowing the exhaust port 7a to face the exhaust gas passage 41 so that the exhaust gas flows without being interfered by the filter 40, and only the flow rate of the outside air can be adjusted by the filter 40. Therefore, an analyzing device can be realized which is simple in structure, capable of preventing leakage as in close emission analysis, and enables open emission analysis to take in outside air.

Additionally, the filter 40 is made of a sponge material which can be elastically deformed easily. Elastically deforming a part of the filter 40 allows it to be connected tightly between the exhaust port 7a and the sampling port 11. Therefore, since there is no attachment and detachment of the emission boots and the connection jig as in the conventional close emission analysis method, the connection of the exhaust port 7a and the sampling port 11 is easily and quickly achieved.

Moreover, forming the filter 40 from a sponge material which changes the air permeability according to the roughness of the sponge material makes it easy to adjust the suppression of the outside air inflow amount by adjusting the roughness of the sponge material. In addition, the setting of the filter is also facilitated because it only requires selecting the roughness of the sponge material constituting the filter from the range of the fine filter to the medium filter shown in FIG. 8.

Further, since the filter 40 is sandwiched between the opening edge portion 14 of the sampling port 11 and the end cap 6a, the mounting of the filter 40 is facilitated and there is no hassle in connecting the sampling port 11 and the peripheral portion of the exhaust port 7a. In addition, the outside air inflow suppressing member 40 can be used commonly for a plurality of members having different shapes, and versatility is enhanced since the emission boot and a special connecting jig are not used, thereby the number of stock members can be reduced.

Furthermore, the flow velocity of the traveling wind flowing around the muffler 6 may vary depending on the position thereof. For example, the flow velocity of the traveling wind is different among the parts of the muffler 6 in the vehicle width direction wherein the inner side is the part near the vehicle body where the flow of the traveling wind is not smooth, and the outer side is the part away from the vehicle body where the flow of the traveling wind is smooth. Due to a significant difference in the flow velocity, there is a possibility that the exhaust gas partially leaks at a portion with a high flow velocity (refer to the aforementioned Patent Literature 1).

However, even in such a case, according to the present exemplary embodiment, the filter 40 is capable of suppressing the traveling wind at this high flow velocity and allowing it to flow thereinto. Therefore, the partial leakage of exhaust gas based on such uneven flow velocity can be effectively coped with in the present exemplary embodiment.

Figure 11:
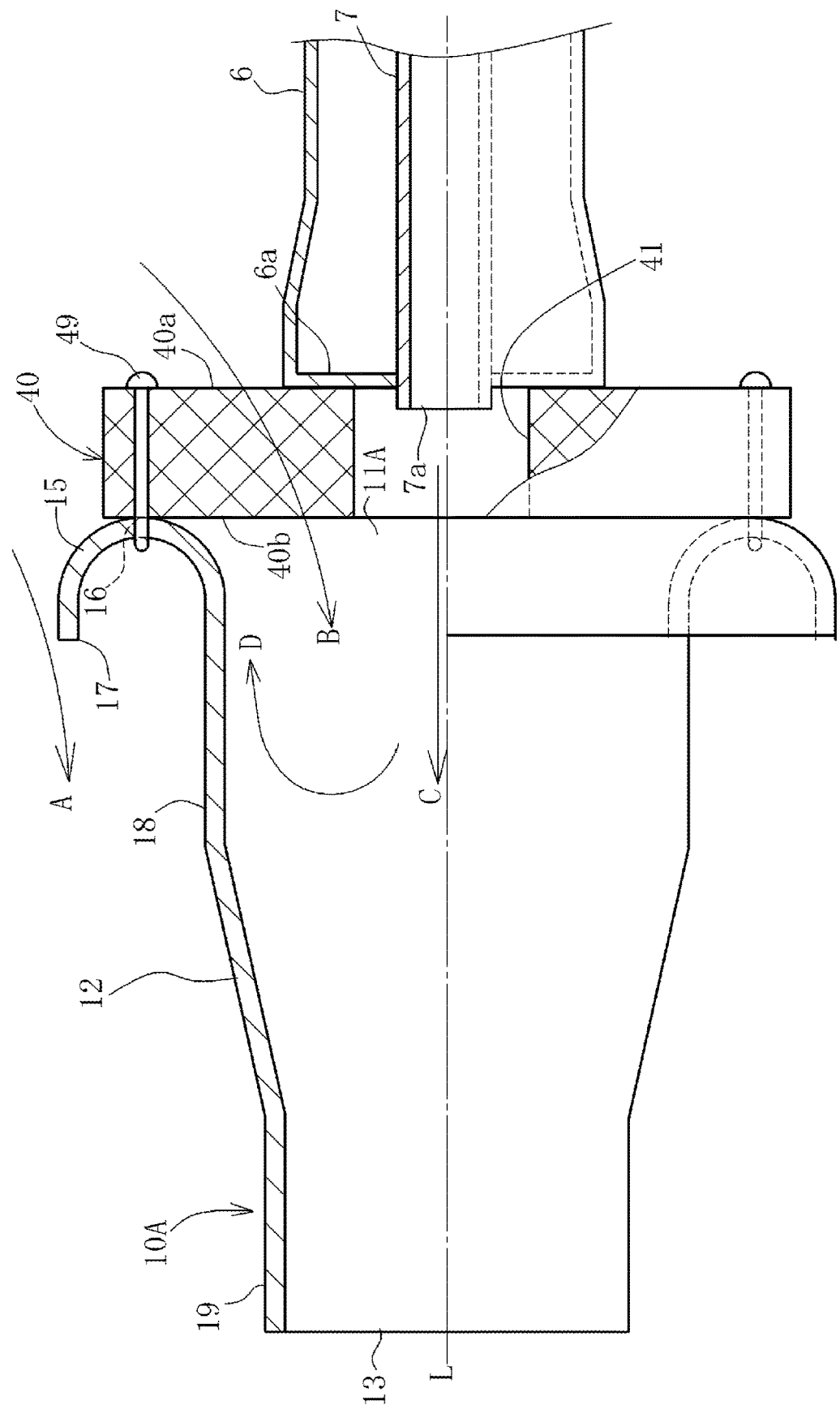
FIG. 11 is a half sectional view of a part similar to FIG. 4 according to a second exemplary embodiment.

Next, a second exemplary embodiment will be described with reference to FIG. 11. FIG. 11 shows a half cross section of the same parts as in FIG. 4.

An exhaust gas sampling unit 10A has a funnel shape with an upstream end portion thereof that includes a curved flange 15. The curved flange 15 corresponds to the curved portion of the present invention and has a substantially U-shaped cross section wherein an uppermost upstream portion 16, which is the most upstream position thereof, provides the opening edge portion of a sampling port 11A. A distal end 17 of the curved flange 15 extends backward over the upstream end portion of the exhaust gas sampling unit 10A.

The exhaust gas sampling unit 10A is provided with straight portions 18 and 19 that are substantially parallel to the central axis line L on the upstream side and the downstream side, respectively, with the intermediate tapered surface 12 interposed therebetween.

The curved flange 15 is integrally formed with the upstream side end portion of the upstream side straight portion 18, and its distal end 17 overlaps the straight portion 18 with a space therebetween. The distal end 17 is larger in diameter than the uppermost upstream portion 16, which is the opening edge portion of the sampling port 11A, and is located downstream of the uppermost upstream portion 16.

A downstream surface 40b of the filter 40 is pressed against the uppermost upstream portion 16 of the curved flange 15. An upstream surface 40a of the filter 40 is pressed by the end cap 6a of the muffler 6, and as a result, the filter 40 is sandwiched between the end cap 6a and the uppermost upstream portion 16 of the curved flange 15. The filter 40 is closely attached to the uppermost upstream portion 16 of the curved flange 15 and the curved flange 15 is utilized as a protrusion for fixing the filter 40.

Furthermore, the outer periphery of the filter 40 is fixed to the curved flange 15 by a fixing member, which in this example is a pin 49. The pin 49 in this example is inserted into the filter 40 from the upstream surface 40a side to the downstream side, and an enlarged head portion of the pin 49 is brought into contact with the upstream surface 40a, whereas the tip end side is passed through a through hole formed in advance in the uppermost upstream portion 16 of the curved flange 15 and folded at the inside of the curved concave of the curved flange 15, thereby being easily mounted.

Note that it is optional to use a fixing member other than the pin 49 shown as the fixing member.

With this configuration in which the filter 40 is fixed to the exhaust gas sampling unit 10A with ease by utilizing the curved flange 15, which is a funnel shaped flange part, as a part for fixing the filter 40, and by forming the curved flange 15 into an arc shape in which the inner diameter side of the uppermost upstream portion 16 forms a rounded slope that is inclined toward the center of the sampling port 11A, the exhaust gas sampling unit 10A can smoothly take in the outside air. Further, since the outer diameter side of the uppermost upstream portion 16 also forms a rounded slope that protrudes forward, a portion of the traveling wind is caused to flow smoothly to the outside of the exhaust gas sampling unit 10A, thereby preventing the occurrence of turbulence in the vicinity of the sampling port 11A.

It is to be noted that the present invention is not limited to the embodiments described above but various modifications thereof can made. For example, the adjustment of the flow rate of the outside air entering the exhaust gas sampling unit 10 through the filter 40 is performed by adjusting the air-flow resistance of the filter 40. The air-flow resistance can be freely adjusted depending on the material, thickness, degree of communication, etc. of the filter 40.

Moreover, since the filter 40 is made of an elastic sponge-like material, due to its elastic deformation, even if the muffler is irregular in shape, the filter 40 is capable of closely covering the space between the exhaust gas sampling unit 10 and the exhaust port 7a, without having to make exclusive ones for each shape of the muffler or the like. Therefore, one filter 40 can be commonly used for various shapes of the muffler 6 and the exhaust port 7a, and the versatility is enhanced.

Hereinafter, examples of various shapes of the muffler 6 and the exhaust port 7a will be described with reference to FIGS. 12A-12D.

The variations are illustrated in FIGS. 12A to 12D. In each of the variation, a schematic side sectional view centered on the filter portion is illustrated on the left side, and the shapes of the filter 40, the muffler 6 and the exhaust port 7a in the axial view are schematically illustrated on the right side.

First, in FIG. 12A, the end cap 6a of the muffler 6 has an inclined surface sloping downward toward the downstream side. Without protruding from the center of the end cap 6a, a rear end portion 7b of the tail pipe 7 is in a position retracted into the muffler 6. An exhaust port 6b is a portion facing the through hole 41 of the end cap 6a and is formed by opening a portion on the extension of the tail pipe 7. Note that the structure in which the exhaust port 6b is provided in the end cap 6a is common in the following structures of FIGS. 12B to 12D.

Even if the end cap 6a is inclined as described above, upon pressing the end cap 6a against the filter 40, the filter 40 is elastically deformed along the end cap 6a due to the fact that the filter 40 is an elastic member, and therefore the periphery of the exhaust port 6b can be closed tightly with the filter 40. The filter 40, the end cap 6a, and the exhaust port 6b are concentrically arranged. The same is true for the structure in FIG. 12B.

FIG. 12B shows an example in which the end cap 6a is at a right angle relative to the filter 40. Likewise, in this case, by pressing the rear end of the end cap 6a against the filter 40, the filter 40 can be elastically deformed and the periphery of the exhaust port 6b can be closed tightly with the filter 40.

FIG. 12C shows an example in which the end cap 6a of the muffler 6 has an inclined surface and is of a substantially triangular shape as viewed in the axial direction. Even with the end cap 6a having such an irregular shape, if pressed against the filter 40, the filter 40 is elastically deformed along the outer periphery of the end cap 6a, and the periphery of the exhaust port 6b can be closed tightly with the filter 40. As viewed in the axial direction, the filter 40 and the exhaust port 6b are respectively circular in shape and arranged concentrically. The end cap 6a has the center of the exhaust port 6b aligned with the axis of the filter 40. Note that the through hole 41 of the filter 40 has a size that allows the end cap 6a to be overlapped with the periphery.

FIG. 12D shows an example of a configuration provided with the end cap 6a of the muffler 6 having the same irregular shape as that of FIG. 12C, a plurality of tail pipes 7 (two, in this example), and a plurality of the exhaust ports 6b corresponding to the number of tail pipes (two, in this case). Even in this case, the filter 40 is capable of tightly closing the exhaust port 6b.

Note that although the filter 40 and the exhaust port 6b are each circular in shape in the axial directional view, the end cap 6a is provided such that the center thereof is deviated from the axis of the filter 40, and the two exhaust ports 6b are also deviated from the axis of the filter 40. In this case, the through hole 41 is also formed to deviate from the axis of the filter 40, and two exhaust ports 6b are inserted into the through hole 41. The through hole 41 has a size that allows the end cap 6a to be overlapped with the periphery.

Furthermore, the outside air inflow suppressing member of the present invention is not limited to the above described sponge-like filter, and various configurations are possible. For example, the material may be formed into blocks having air permeability and easy shape deformation using fibers such as metal fibers, mineral fibers and plant fibers. The material may be a multi-layered cloth or paper, etc. including nonwoven fabric.

Further, the material may be a hollow bodies having air permeability and filled with fibers, powder, or granules. In short, any material may be used as long as it has air permeability, is capable of suppressing the flow rate of fluid passing by air-flow resistance, and additionally, has some elasticity, and can easily deform and adhere tightly in accordance with the member to be attached with.

A material that easily deforms its shape is preferably one that deforms so as to be easily pushed in the pressing direction when a predetermined pressure is applied at the time of attachment or the like and is elastically deformed so as to return to its original shape when pressure is removed.

In addition, the outside air inflow suppressing member may not be a plate like the filter of the present exemplary embodiment but may have a cylindrical shape as shown in FIG. 6B. In this case, the opening side at one end faces the exhaust port whereas the other end opening side covers the inside or outside of the sampling port.

REFERENCE SIGNS LIST

1 . . . Open Emission Analysis System
2 . . . motorcycle
4 . . . exhaust pipe
6 . . . muffler
6a . . . end cap
6b . . . exhaust port
7 . . . tail pipe
7a . . . exhaust port
10, 10A . . . exhaust gas sampling unit
11, 11A . . . sampling port
15 . . . curved portion
40 . . . filter (outside air inflow suppressing member)
41 . . . through hole
44 . . . exhaust gas passage

The invention claimed is:

1. An open emission analysis method comprising:
taking in exhaust gas discharged from an exhaust port together with ambient outside air from an exhaust gas sampling unit;
analyzing the collected exhaust gas;
covering an outside air inflow gap by an air-permeable outside air inflow suppressing member located between a sampling port of the exhaust gas sampling unit and a periphery of the exhaust port; and
suppressing inflow of the outside air by the outside air inflow suppressing member in order to prevent leakage of the exhaust gas from the sampling port.

2. The open emission analysis method according to claim 1, further comprising:
suctioning the exhaust gas sampling unit at a predetermined suction flow rate, and
suppressing the total inflow flow rate of the exhaust gas and the outside air flowing into the sampling port to be less than the suction flow rate by using the outside air inflow suppressing member.

3. The open emission analysis method according to claim 2, wherein
the outside air inflow suppressing member allows the exhaust gas to flow without interfering and the outside air to pass through while suppressing the speed of the air by air-flow resistance.

4. An open emission analysis device comprising:
an exhaust gas sampling unit for taking in exhaust gas discharged from an exhaust port located at a rear end portion of a muffler together with ambient outside air;
a quantitative flow path for flowing a mixed gas of the collected exhaust gas and outside air at a constant flow rate;
a suction means for sucking the quantitative flow path at a predetermined suction flow rate;
a concentration analyzing unit for analyzing the exhaust gas with respect to the mixed gas in the quantitative flow path; and
an air-permeable outside air inflow suppressing member configured to cover an outside air inflow gap located between a sampling port of the exhaust gas sampling unit and a periphery of the exhaust port,
wherein the outside air inflow suppressing member passes the outside air therethrough to the sampling port.

5. The open emission analysis device according to claim 4, wherein
the outside air inflow suppressing member is a filter covering the sampling port and has a through hole serving as an exhaust gas passage, and the exhaust port faces the through hole.

6. The open emission analysis device according to claim 5, wherein
the muffler includes an end cap covering a rear end portion thereof, and
the outside air inflow suppressing member is disposed between the sampling port and the end cap.

7. The open emission analysis device according to claim 6, further comprising
a curved portion that is a turned-back edge portion of the sampling port,
wherein the outside air inflow suppressing member is disposed between the curved portion and the end cap.

8. The open emission analysis device according to claim 4, wherein
the outside air inflow suppressing member is made of a material that is deformable in shape.

9. The open emission analysis device according to claim 5, wherein
the filter is made of a sponge material whose air permeability changes according to the roughness of the sponge material.

10. The open emission analysis device according to claim 9, wherein
the roughness of the sponge material renders the total inflow flow rate of the exhaust gas and the flow rate of the outside air flowing into the sampling port to be set less than the suction flow rate in an entire measurement range.

* * * * *